(12) United States Patent
Barakat et al.

(10) Patent No.: US 12,318,117 B2
(45) Date of Patent: Jun. 3, 2025

(54) ROBOTIC ANATOMICAL MANIPULATION SYSTEMS AND METHODS

(71) Applicant: Memorial Sloan Kettering Cancer Center, New York, NY (US)

(72) Inventors: Richard Barakat, Muttontown, NY (US); Paul Booth, New York, NY (US); Charles Kim, Lewisburg, PA (US); Kelsey Ann Tacca, Munich (DE); Jordan Anthony Rivera, Fairport, NY (US); Samuel Thomas Pratt, Hudson, OH (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 668 days.

(21) Appl. No.: 17/601,322

(22) PCT Filed: Apr. 3, 2020

(86) PCT No.: PCT/US2020/026636
§ 371 (c)(1),
(2) Date: Oct. 4, 2021

(87) PCT Pub. No.: WO2020/206297
PCT Pub. Date: Oct. 8, 2020

(65) Prior Publication Data
US 2022/0192707 A1    Jun. 23, 2022

Related U.S. Application Data

(60) Provisional application No. 62/829,311, filed on Apr. 4, 2019.

(51) Int. Cl.
*A61B 17/42* (2006.01)
*A61B 17/00* (2006.01)
(Continued)

(52) U.S. Cl.
CPC .......... *A61B 17/4241* (2013.01); *A61B 34/30* (2016.02); *A61B 90/03* (2016.02);
(Continued)

(58) Field of Classification Search
CPC ..... A61B 17/4241; A61B 34/30; A61B 90/03; A61B 2034/742; A61B 2090/066;
(Continued)

(56) References Cited

U.S. PATENT DOCUMENTS 8,423,182 B2    4/2013  Robinson et al.
8,601,897 B2    12/2013 Lauzier et al.
(Continued)

FOREIGN PATENT DOCUMENTS

KR    101358668 B1    2/2014
KR    101757881 B1    7/2017
(Continued)

OTHER PUBLICATIONS

International Search Report, PCT/US2020/026636, Jun. 12, 2020.
(Continued)

*Primary Examiner* — Tan-Uyen T Ho
*Assistant Examiner* — Cherie M Poland
(74) *Attorney, Agent, or Firm* — Eleanor Musick; Torrey Pines Law Group PC

(57) ABSTRACT

The present invention provides, in various embodiments, systems and methods for robotic manipulation of a patient's anatomy, such as the uterus, during surgical procedures.

21 Claims, 24 Drawing Sheets

(51) Int. Cl.
*A61B 34/00* (2016.01)
*A61B 34/30* (2016.01)
*A61B 90/00* (2016.01)
*B25J 5/00* (2006.01)
*B25J 13/06* (2006.01)
*B25J 13/08* (2006.01)
*B25J 19/06* (2006.01)

(52) U.S. Cl.
CPC ............ *B25J 5/007* (2013.01); *B25J 13/065* (2013.01); *B25J 13/085* (2013.01); *B25J 19/061* (2013.01); *A61B 2017/00119* (2013.01); *A61B 2017/00199* (2013.01); *A61B 2017/00477* (2013.01); *A61B 2017/4216* (2013.01); *A61B 2034/742* (2016.02); *A61B 2090/066* (2016.02); *A61B 2090/0807* (2016.02)

(58) Field of Classification Search
CPC .. A61B 2090/0807; A61B 2017/00119; A61B 2017/00199; A61B 2017/00477; A61B 2017/4216; B25J 5/007; B25J 13/065; B25J 13/085; B25J 19/061
See application file for complete search history.

(56) References Cited

U.S. PATENT DOCUMENTS

| | | |
|---|---|---|
| 8,845,622 B2 | 9/2014 | Paik et al. |
| 8,961,499 B2 | 2/2015 | Paik et al. |
| 9,375,206 B2 | 6/2016 | Vidal et al. |
| 9,554,859 B2 | 1/2017 | Nowlin et al. |
| 9,687,310 B2 | 6/2017 | Nowlin et al. |
| 9,700,337 B2 | 7/2017 | Vidal et al. |
| 9,827,059 B2 | 11/2017 | Robinson et al. |
| 9,867,671 B2 | 1/2018 | Kumar et al. |
| 9,895,813 B2 | 2/2018 | Blumenkranz et al. |
| 10,278,783 B2 | 5/2019 | Itkowitz et al. |
| 10,582,977 B2 | 3/2020 | Morel et al. |
| 10,639,066 B2 | 5/2020 | Vidal et al. |
| 10,765,412 B2 | 9/2020 | Rosa et al. |
| 10,820,949 B2 | 11/2020 | Prisco et al. |
| 10,905,505 B1 | 2/2021 | Barakat et al. |
| 2009/0248038 A1* | 10/2009 | Blumenkranz ........ A61B 34/30 606/130 |
| 2010/0331859 A1 | 12/2010 | Omori |
| 2014/0039681 A1* | 2/2014 | Bowling ................ A61B 34/30 700/261 |
| 2016/0121491 A9* | 5/2016 | Lauzier .................. B25J 9/0048 901/46 |
| 2016/0235490 A1* | 8/2016 | Srivastava ............. A61B 34/30 |
| 2017/0112535 A1 | 4/2017 | Ahluwalia |
| 2017/0113535 A1 | 4/2017 | Hirano |
| 2019/0060155 A1 | 2/2019 | Corrigan et al. |
| 2019/0201018 A1* | 7/2019 | Shelton, IV ........... G16H 40/20 |

FOREIGN PATENT DOCUMENTS

| | | |
|---|---|---|
| WO | 2011037718 A1 | 3/2011 |
| WO | 2015154172 A1 | 10/2015 |
| WO | 2018013965 A1 | 1/2018 |

OTHER PUBLICATIONS

Akrivos, N., et al., A pilot study of robotic uterine and vaginal vault manipulation: The ViKY Uterine Positioner, Journal of Robotic Surgery, Apr. 2013, 7:371-375.

VIKY by Endocontrol, Motorized Endoscope Positioner, Brochure, updated Jun. 2017.

Man, Yip Hiu et al., A New Robotic Uterine Positioner for Laparoscopic Hysterectomy with Passive Safety Mechanisms: Design and Experiments, 2015 IEEE/RSJ International Conference on Intelligent Robots and Systems (IROS), IEEE, Sep. 28, 2015, pp. 3188-3194.

EP Appl. No. 20784160.2 Supplementary European Search Report & Written Opinion, Nov. 29, 2022, 10 pages.

* cited by examiner

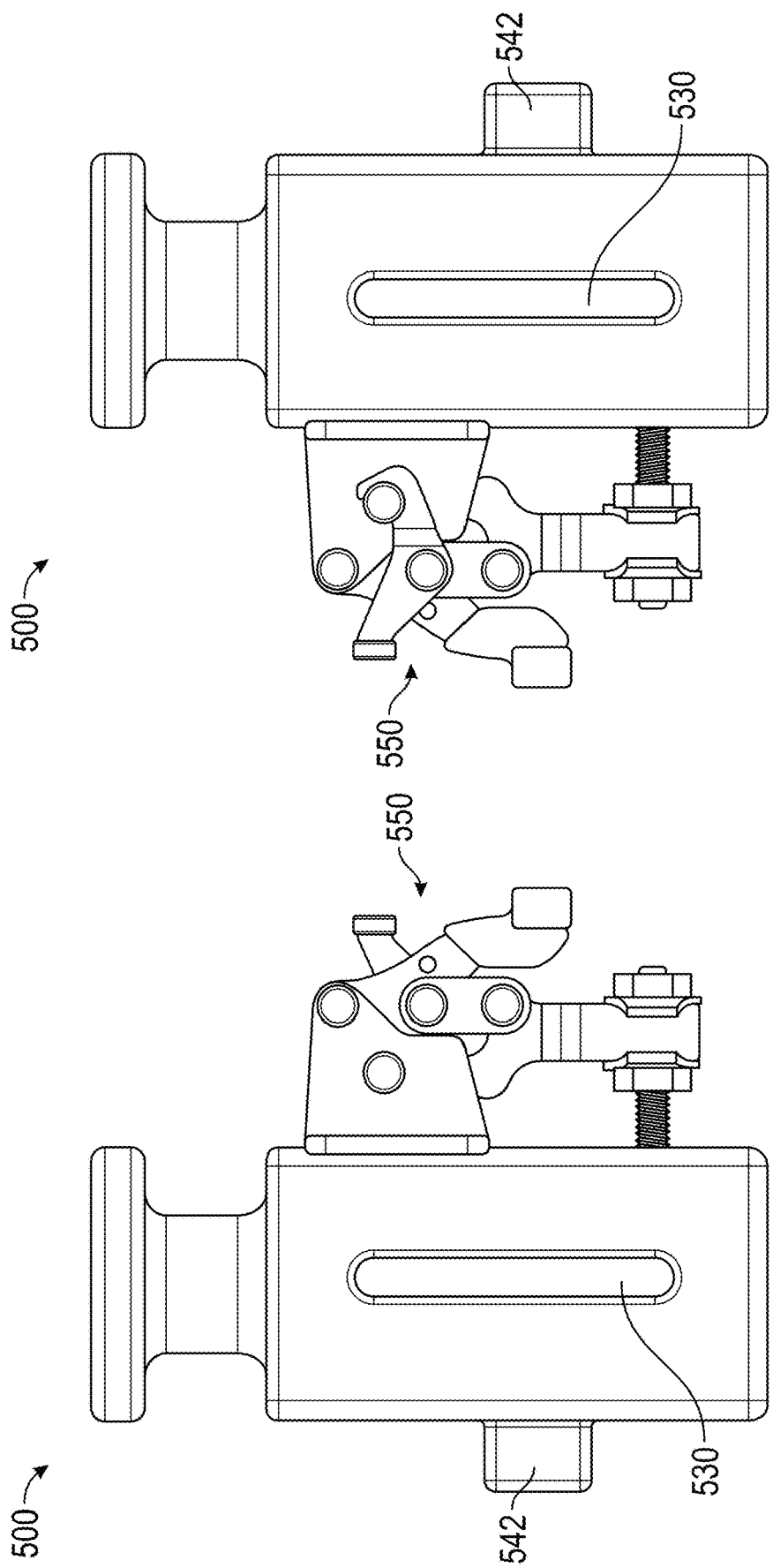

| TOP-LEVEL ITEM | MID-LEVEL ITEM | SOFTWARE UNIT | DESCRIPTION | SOUP |
|---|---|---|---|---|
| LABVIEW CONTROL | UR5 LABVIEW CONTROL | CONTROL | CENTRAL COORDINATION OF THE LABVIEW UNITS. UNIT RECEIVES USER INPUT FROM THE KINEMATICS UNIT, FORCE TORQUE READ, USER INTERFACE THROUGH DISPLAY AND GENERATES THE COMMANDS TO THE ROBOT. | NO |
| | | KINEMATICS | CONVERTS JOYSTICK INPUTS INTO UTERINE MANIPULATOR MOVEMENT. | NO |
| | | FORCE TORQUE READ | MONITORS FORCE TORQUE SENSOR AND RESTRICTS UTERINE MANIPULATOR MOVEMENT BASED ON FORCE TORQUE SENSOR VALUES. | NO |
| | | TCP/IP READ | READS UR5 STATE USING UR5 REAL-TIME COMMUNICATIONS INTERFACE. | NO |
| | | TCP/IP WRITE | WRITES COMMANDS TO UR5 USING URSCRIPT PROGRAMMING LANGUAGE. | NO |
| | | LABVIEW | REAL-TIME PROCESSING PLATFORM FOR ACQUISITION, CALCULATION, AND CONTROL. | YES |
| | | JOYSTICK FIRMWARE | FIRMWARE IN THE JOYSTICK TRANSLATES POSITION INTO ELECTRICAL SIGNALS. | YES |
| | | TOUCHSCREEN FIRMWARE | FIRMWARE IN THE TOUCHSCREEN PROVIDES CONTROL AND TOUCH PROCESSING. | YES |
| | | NI MODULE FIRMWARE | FIRMWARE IN THE NI DIGITAL OUTPUT MODULE. | YES |

| TOP-LEVEL ITEM | MID-LEVEL ITEM | SOFTWARE UNIT | DESCRIPTION | SOUP |
|---|---|---|---|---|
| EMBEDDED /SAFETY SYSTEM | MAIN LOOP | MAIN | INFINITE LOOP THAT PROVIDES TIME-BASED FUNCTIONALITY AND COORDINATION FOR OTHER UNITS. | NO |
| | GPIO | GPIO | ACQUIRE AND CONDITIONS DIGITAL INPUTS FROM ENABLE/DISABLE SWITCH. | NO |
| | FORCE | FORCE CALCULATION | CONVERTS MEASURED VOLTAGES FROM FT SENSOR TO FORCE/TORQUE MEASUREMENTS. | NO |
| | | ADC UNIT | ACQUIRES VOLTAGE READINGS FROM EACH OF THE 6 CHANNELS OF FORCE AND TORQUE GENERATED BY THE FORCE-TORQUE SENSORS. | NO |
| | ROBOT RELAY CONTROL | ROBOT RELAY CONTROL | PROVIDES CONTROL OF THE UR5 ROBOT POWER RELAY. THE DIGITAL I/O OUTPUT CAN ENABLE/DISABLE THE ROBOT BY CONNECTING/REMOVING POWER FROM THE SYSTEM. | NO |
| UR5 SOFTWARE SYSTEM | MAIN CONTROLLER | MAIN CONTROLLER | COORDINATED MOTION CONTROL OF THE UR5 ROBOTIC ARM. | YES |
| | SAFETY CONTROLLER | SAFETY CONTROLLER | SUPERVISORY FIRMWARE ON THE MOTION CONTROL OUTPUTS OF THE UR5 MAIN CONTROLLER. FIRMWARE RECEIVES ENABLE/DISABLE INPUTS AND EMERGENCY STOP. FIRMWARE CONTROLS POWER OUTPUT TO MOTOR CONTROLLER. | YES |

FIG. 14

X- Direction

Y- Direction

ROBOTIC ANATOMICAL MANIPULATION SYSTEMS AND METHODS

RELATED APPLICATIONS

This application is a 371 national stage filing of International Application No. PCT/US2020/026636, filed Apr. 3, 2020, which claims the benefit of U.S. application Ser. No. 62/829,311, filed Apr. 4, 2019, each of which is incorporated by reference herein in its entirety.

COMPUTER PROGRAM LISTING APPENDIX

A computer program listing comprising a single ASCII text file titled "Kinematics Code.txt" was submitted electronically and is incorporated by reference herein in its entirety.

BACKGROUND

In gynecologic surgical procedures such as hysterectomies, the patient's uterus needs to be positioned precisely according to the specific requirements of the case throughout the surgery. Improved systems and methods for uterine manipulation are needed in the art.

SUMMARY

The present disclosure relates generally to robotic anatomical manipulation systems and methods, and more specifically, to robotic uterine manipulation systems and methods for use in minimally invasive hysterectomies.

In various embodiments, the invention provides robotic anatomical manipulation system for use with an end effector configured to position and hold an anatomy of a patient during a minimally invasive surgical procedure, the system comprising: a robot comprising a cart and an arm, a proximal end of the arm connected to the cart; a console comprising a joystick and a user interface, the joystick configured to provide real-time motion inputs to the arm; a mechanical interface connected to a distal end of the arm and configured to hold and release a proximal end handle of the end effector; a sensor positioned between the distal end of the arm and the mechanical interface, the sensor configured to measure at least one of force and torque generated by the end effector; and a non-transitory computer readable medium having stored thereon computer executable code for a control system controlling the arm responsive to user input through the joystick and the user interface. The end effector has a substantially curved body, a distal end tip, and an adjustable fulcrum configured to be positioned at a distance relative to the tip that is specific for each patient in each surgical procedure. The control system includes a kinematics unit configured to determine motion of the arm required to produce user-specified motion of the tip, based on the curvature of the end effector and the patient-specific fulcrum position input to the user interface. The control system also includes a force torque read unit configured to monitor the sensor and, when a predetermined force threshold or torque threshold is reached in a direction, to send a stop signal to the arm to prevent motion in that direction. In some embodiments, the anatomy is a uterus and the minimally invasive surgical procedure is a robotically-assisted or manual laparoscopic hysterectomy.

The cart may be mobile or stationary. The console is in communication with the remote machine via a wired connection or a wireless connection. In some embodiments, the console further comprises a video feed configured to display a live signal from a camera used to monitor the surgical procedure.

In some embodiments, the arm comprises six joints: base (A), shoulder (B), elbow (C), and wrist (D, E, F). In some embodiments, the elbow is positioned below the wrist in a baseline position. In some embodiments, the arm comprises at least one joint having markings thereon, the markings indicating safe ranges for a baseline position.

In some embodiments, the mechanical interface includes a quick release mechanism configured to release the end effector within five seconds without moving the robot arm or cart.

In some embodiments, the sensor is a three-axis force and torque sensor configured to acquire six channels of force and torque: Fx, Fy, Fz, Tx, Ty, and Tz.

In some embodiments, the force threshold is a warning force threshold and the torque threshold is a warning torque threshold. In some embodiments, the warning force threshold is 10 lbf and the warning torque threshold is 70 in-lbs.

In some embodiments, the non-transitory computer readable medium having further stored thereon computer executable code for an embedded safety system calculating the force and torque generated by the end effector, wherein the embedded safety system is configured to generate a digital disable command to disable all control of the arm until the system is manually re-enabled, if a predetermined safety force threshold or safety torque threshold is exceeded.

In some embodiments, the embedded safety system comprises an analog-to-digital converter (ADC) unit configured to acquire force and torque data from the sensor at least 100 times per second.

In some embodiments, the embedded safety system further comprises a force unit configured to receive raw voltages communicated by the sensor to the ADC unit, and to convert the raw voltages to force and torque values.

In some embodiments, the safety force threshold is 12 lbf and the safety torque threshold is 90 in-lbs.

In some embodiments, the console includes a mechanism to enable/disable control of the arm from the joystick and the user interface, and wherein the embedded safety system is configured to capture enable/disable input and generate a command to the robot responsive thereto.

In some embodiments, the user interface includes a stop axis indicator configured to provide a visual indication of which axis the predetermined safety force threshold or safety torque threshold is exceeded on.

In some embodiments, the cart includes a setup positioning system on an upper surface thereof, the proximal end of the arm connected to the setup positioning system, and the setup positioning system configured to provide forward and reverse translation in the X, Y, and Z directions.

In some embodiments, the console includes an alarm providing an audible indication of at least one of movement and speed of the distal end of the arm.

Additional features and advantages of the present invention are described further below. This summary section is meant merely to illustrate certain features of the invention, and is not meant to limit the scope of the invention in any way. The failure to discuss a specific feature or embodiment of the invention, or the inclusion of one or more features in this summary section, should not be construed to limit the invention as claimed.

BRIEF DESCRIPTION OF THE DRAWINGS

The foregoing summary, as well as the following detailed description of various embodiments of the application, will be better understood when read in conjunction with the appended drawings. For the purposes of illustrating the systems and methods of the present application, there are shown in the drawings certain embodiments. It should be understood, however, that the application is not limited to the precise arrangements and instrumentalities shown. In the drawings:

FIGS. 5A-5H are front perspective, back perspective, front, back, left side, right side, top, and bottom views, respectively, of a mechanical interface, according to various embodiments of the invention;

FIG. 14 is a table of the individual software units for each software item;

DETAILED DESCRIPTION

Figure 1A:
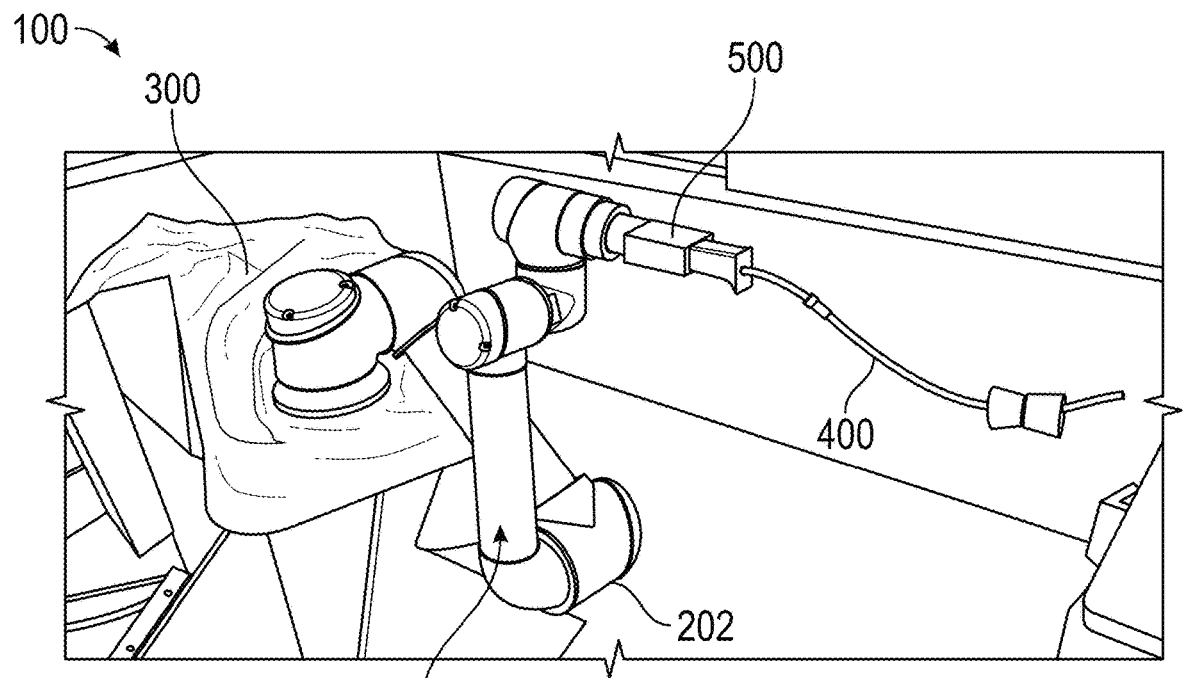
FIG. 1A is a perspective view of a robotic uterine manipulation system, according to various embodiments of the invention.

In a minimally invasive (robotic-assisted or manual laparoscopic) gynecologic procedure such as a hysterectomy, the patient's uterus needs to be positioned precisely according to the specific requirements of the case throughout the surgery. Uterine manipulation is an important component of a successful minimally invasive hysterectomy, wherein the anatomy is manipulated, for example, to tilt and/or displace the uterus for safe dissection of the ureter, suspensory ligaments of the uterus, and the uterine blood supply.

The current standard of practice is for a surgical resident or fellow, taking positional instructions from the operating surgeon, to manipulate the uterus manually using one or more handheld tools. Over the course of the surgery, this practice can present significant physical challenges, as the resident or fellow often has to maneuver themselves around other equipment used in the surgery, such as the large footprint of a surgical robot. This practice can be difficult, as the individual manipulating the uterus may be situated at an awkward angle or to the side of the perineum. It can also be physically demanding.

The present invention overcomes such problems and provides, in various embodiments, robotic anatomical manipulation systems and methods for surgical procedures, which can provide more accurate and precise manipulation and positioning of the subject anatomy, as compared to the current standard of practice. Using the robotic anatomical manipulation systems and methods according to embodiments of the present invention, the surgeon can control the position of the anatomy from a control console away from the operating table and away from any surgical robot equipment/separate surgical robot control console, if present. The surgeon can more precisely adjust the manipulation instruments and the anatomy of the patient to exactly the desired positions and can yield a superior surgical result.

System Hardware

Embodiments of the present invention provide robotic anatomical manipulation systems comprising a robot and a console. The robot may comprise, for example, a cart, an arm (e.g., with six degrees of freedom), and arm support hardware, including a computer and a power supply. The cart is a mobile or stationary unit that the arm resides on. The arm holds and positions a separate end effector. A mechanical interface connects the end effector to the arm. The console may comprise, for example, a joystick (or other input device), a user interface, an enable/disable button, and a video feed, which may be integrated into one unit that is used to interface with the arm. The joystick is used to provide real-time motion inputs to the arm. As used herein, the term "joystick" refers to a control column/stick that pivots on a base (optionally including one or more buttons, switches, triggers, scroll wheels, etc.) or any other input/control device currently known or to be developed, which is configured to provide substantially similar control functions. The user interface provides the user with feedback on the status of the arm and provides means to input configuration parameters. The video feed displays a live signal from a camera used to monitor the surgery.

The robot is configured to be positioned near the operating table (e.g., at the foot of the table for gynecologic surgical procedures). In some embodiments, the console may be positioned near the robot in the operating room, and connected by a wired or wireless connection. In other embodiments, the console may be located remotely from the robot (e.g., in another room or at another geographical location), and connected by a wireless connection.

Figure 1B:
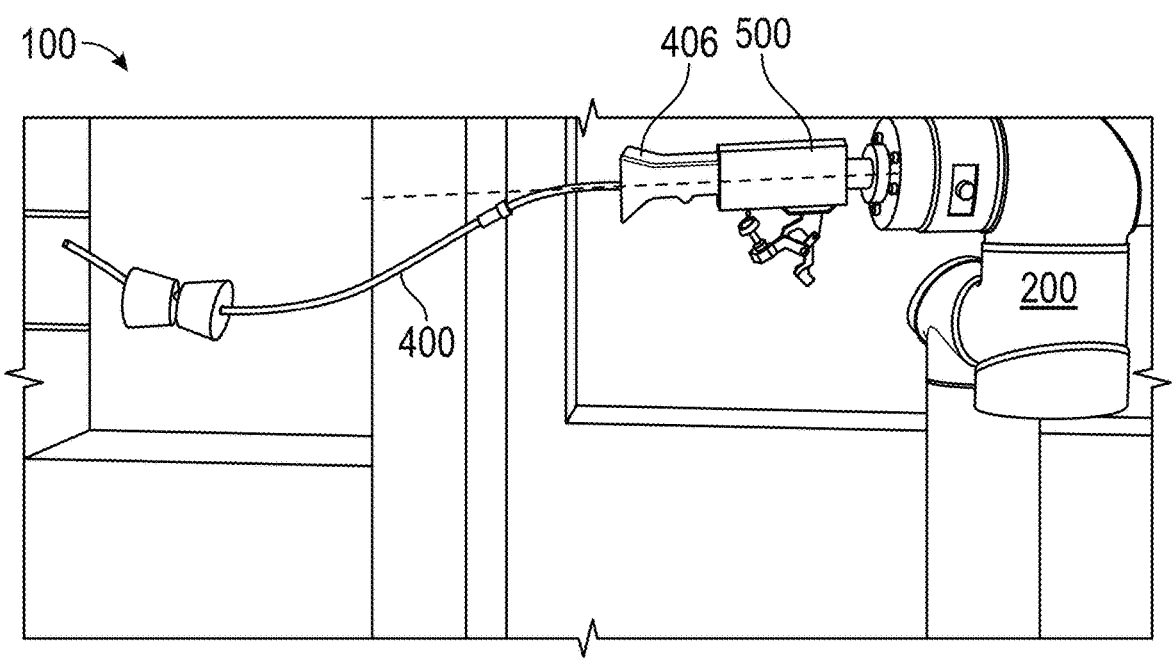
FIG. 1B is a side view of the uterine manipulation system of FIG. 1A, in a baseline position, according to various embodiments of the invention.

FIG. 1A is a perspective view of a robotic uterine manipulation system 100 according to an illustrative embodiment of the present invention. A robotic arm 200, which may be covered in whole or in part by a drape 300, holds and positions a uterine manipulator 400, which is the patient interface end effector. A custom mechanical interface 500 connects the uterine manipulator 400 to the arm 200 and supports the kinematics and other specifications of the uterine manipulator 400 when in use. A sensor (not shown; see FIG. 8) may be positioned between the mechanical interface 500 and the arm 200. FIG. 1B is a side view of the uterine manipulation system of FIG. 1A in a baseline arm position, wherein, according some embodiments, the uterine manipulator 400 is held in a vertical plane with the manipulator handle substantially parallel with the floor and the manipulator tip pointed upward. In some embodiments (e.g., for gynecologic procedures), the elbow of the arm 200 may be positioned below the wrist, as shown in FIG. 1A (e.g., to utilize space below the operating table). In some embodiments, visible markings 202 (e.g., range bars and alignment arrows; see also FIGS. 19A, 19B) may be provided on one or more joints of the arm 200, indicating to the user specific angles and/or safe ranges for a starting position for the surgery or operating range. A safe range may be achieved, for example, if the arrow on each joint is within the band on the other side of the joint. Thus, a surgeon or physician's assistant can manually place the robot arm in a safe/acceptable starting position using the markings 202 as a visual guide (e.g., if the console is not nearby).

Figure 2:
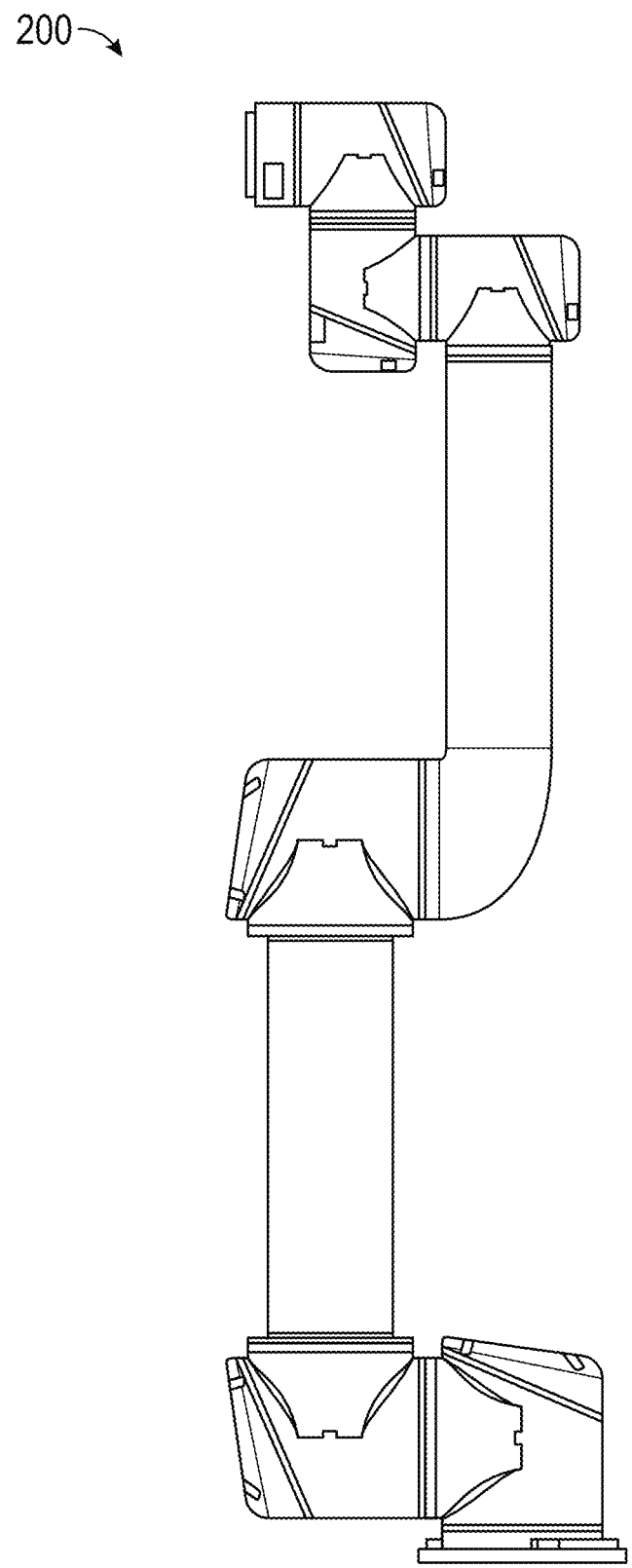
FIG. 2 is a side view diagram of a robotic arm, with dimensions in mm.
Figure 3:
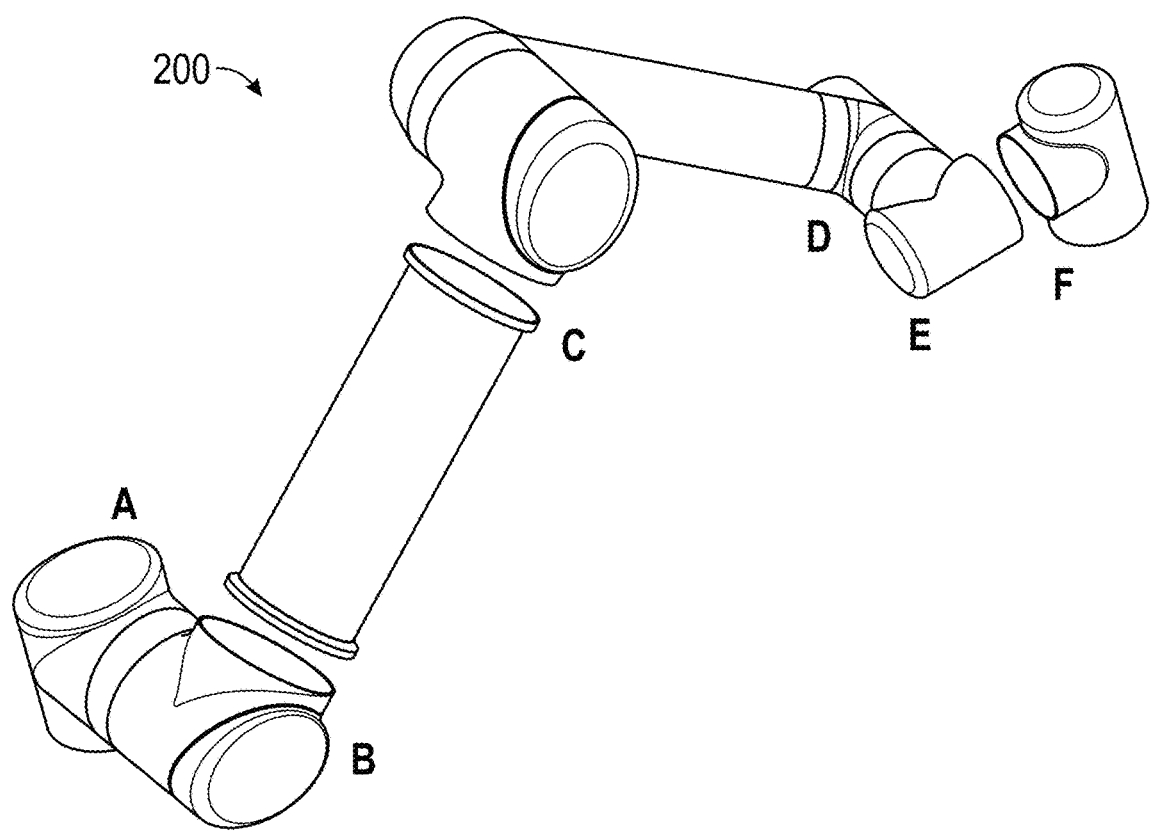
FIG. 3 is a perspective view diagram of the arm of FIG. 2, with six joints labeled.

In some embodiments, the arm 200 comprises a collaborative industrial robotic arm, such as the UR5 from Universal Robots. The UR5 has six rotating joints each with a working range of ±360° and supports a payload of 5 kg (11 lbs), and has a reach of 850 mm (33.5 in). See, e.g., universal-robots.com/media/1801303/eng_199901_ur5_tech_spec_web_a4.pdf for technical specifications. A side view of the UR5 is shown in FIG. 2, indicating its dimensions in mm (diagram taken from universal-robots.com/download/ under Mechanical documentation, UR5 documentation, Robot working area, Robot dimensions area PDF). A diagram of the UR5 is shown in FIG. 3, illustrating the joints of the robot: A (Base), B (Shoulder), C (Elbow), and D, E, F (Wrist 1, 2, 3). See, e.g., Universal Robots User Manual, UR5/CB3, Euromap67, Version 3.5.3, Original instructions (en), US Version. Robot arms such as the UR5 are used in various industries for tasks such as assembly, packaging, etc. However, prior to the present invention, they have not been configured for manipulation of human anatomy in surgical procedures.

Figure 4:
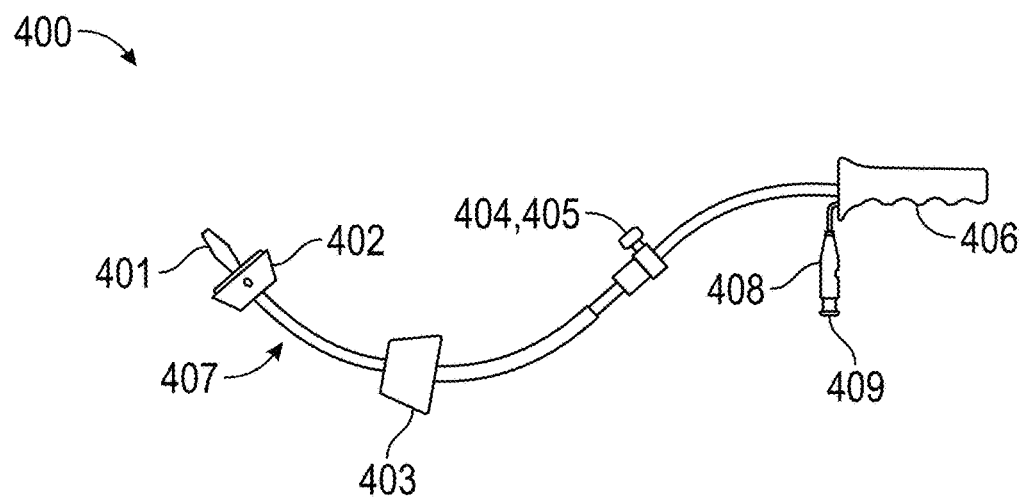
FIG. 4 is a side view diagram of a uterine manipulator.

In some embodiments, the uterine manipulator 400 is a VCare® Vaginal-Cervical Ahluwalia's Retractor-Elevator from ConMed™ Corporation, though other end effectors can be used. The VCare® is a disposable single-use device for manipulation and elevation of the uterus and cervix in surgical and diagnostic procedures. The OD is 5 mm (0.2 in) and the length is 42 cm (16.4 in) including the ergonomic handle 406. A side view of the VCare® is shown in FIG. 4 (diagram taken from Instructions for Use for Product Catalog No. 60-6085-200A at www.conmed.com/en/customer-service/instructions-for-use/eifu-finder). In the VCare® device 400, an insulated manipulator tube 407 is provided that includes visible graduation marks (not shown) to aid in attaining proper depth of insertion, and has a 10-cc inflatable balloon 401 at the patient end. A syringe (not shown) can be attached to an inflation valve 409 on a pilot balloon 408 to inflate the intrauterine balloon 401 with air. The manipulator tube 407 has a natural curved shaft to conform to the patient's anatomy (e.g., the angle of the sacral curve). The graduation marks provide a guide for comparison to a graduated uterine sound (and also indicate a patient-specific distance/fulcrum position, as described in further detail below). The balloon 401 anchors the uterus and stabilizes the shaft within the uterine cavity. The cervical (distal) cup 402 is offered in various sizes (e.g., S, M, L, XL) depending on the size of the patient's cervix. The cervical cup 402 provides a colpotomy guide, and includes holes to suture the cup in place for improved stability of the uterus. The vaginal (proximal) cup 403 can be advanced and locked in position at the back edge of the cervical cup 402 by a slidable locking assembly 404 with thumbscrew 405, to secure the cervical cup 402 and maintain pneumoperitoneum.

In other embodiments, a different robot/arm 200 and/or a different uterine manipulator 400 (or other type of end effector configured to manipulate a different anatomy) may be used, which may be commercially-available or custom-designed. Different end effectors 400 may be selected by the surgeon based on the patient and the needs of each surgery. The mechanical interface 500 can be configured accordingly.

Figure 5A:
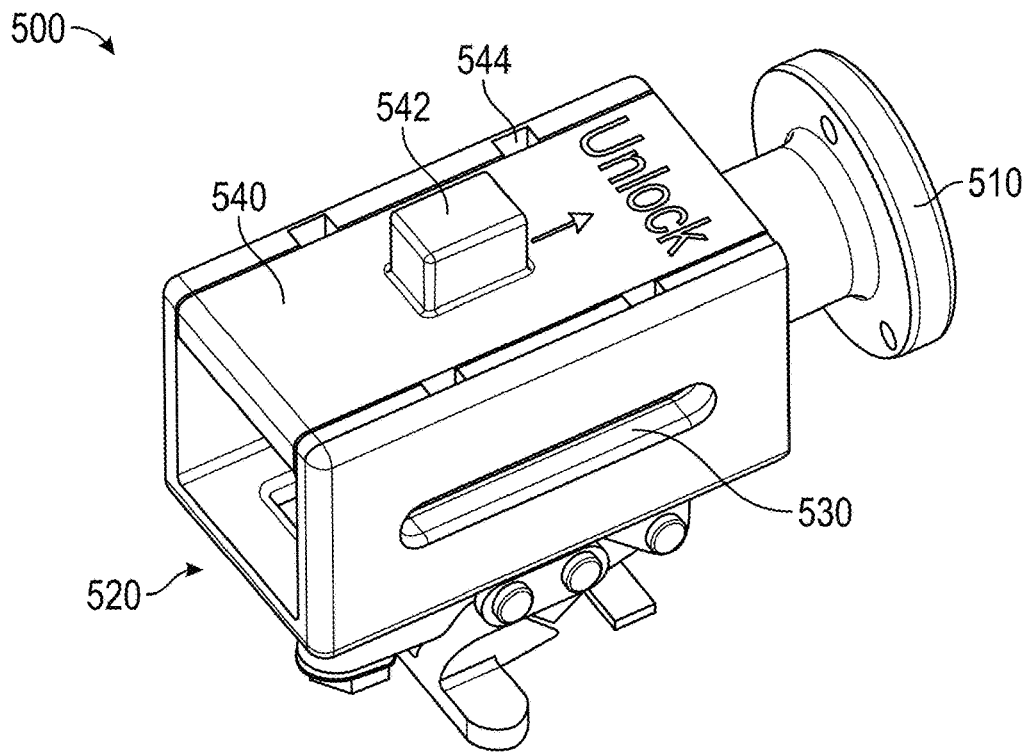
Figure 5B:
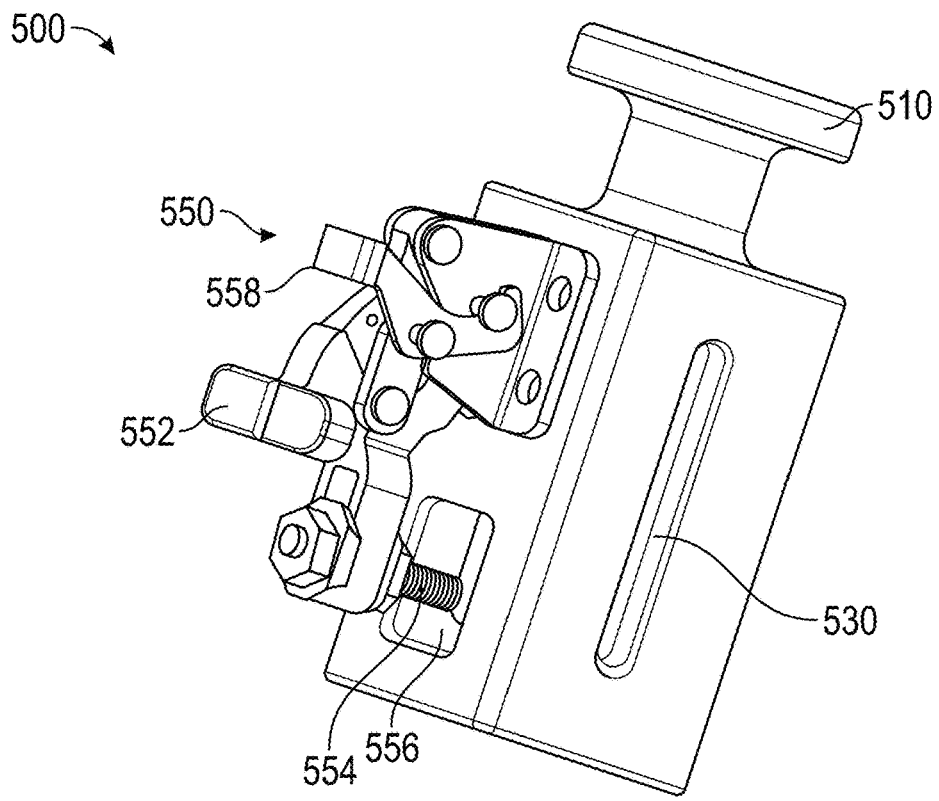
Figure 5D:
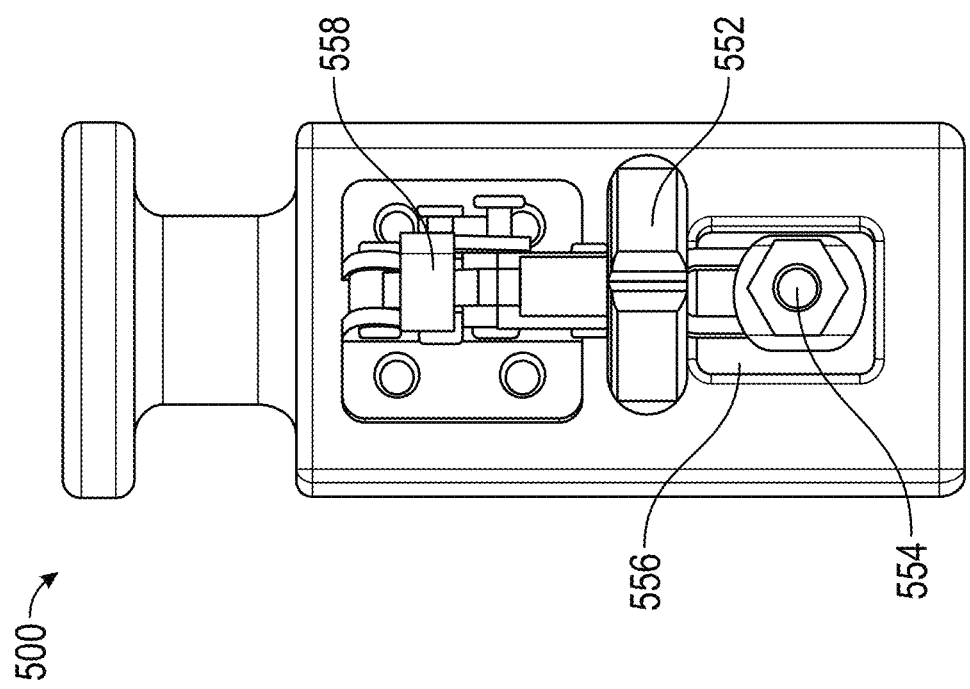
Figure 5C:
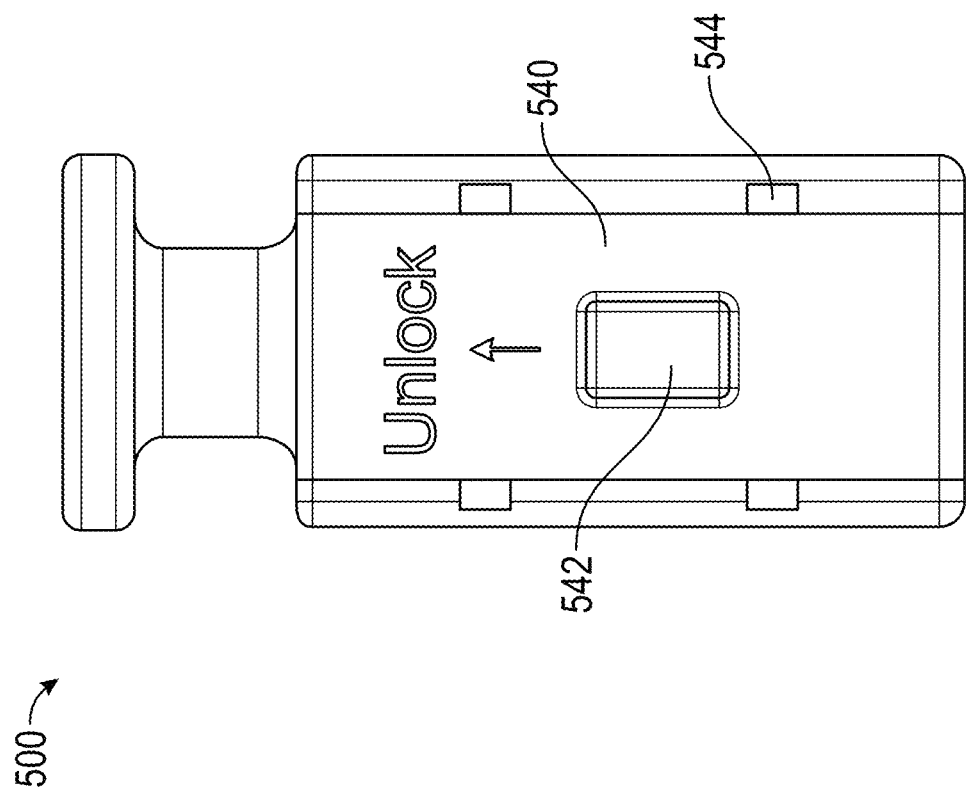
Figure 5G:
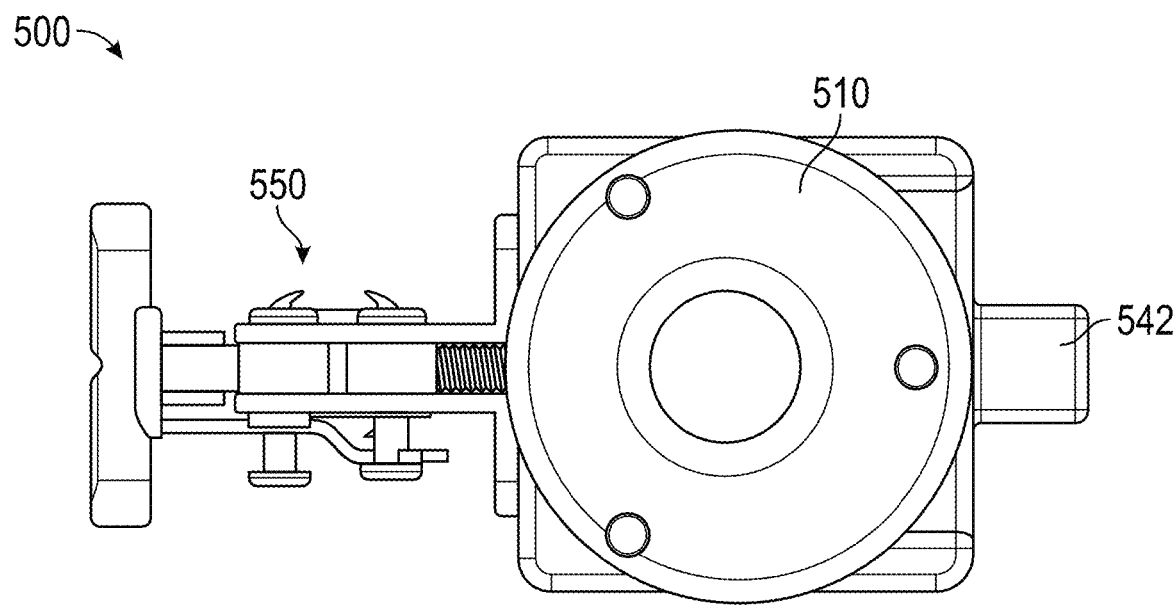
Figure 5H:
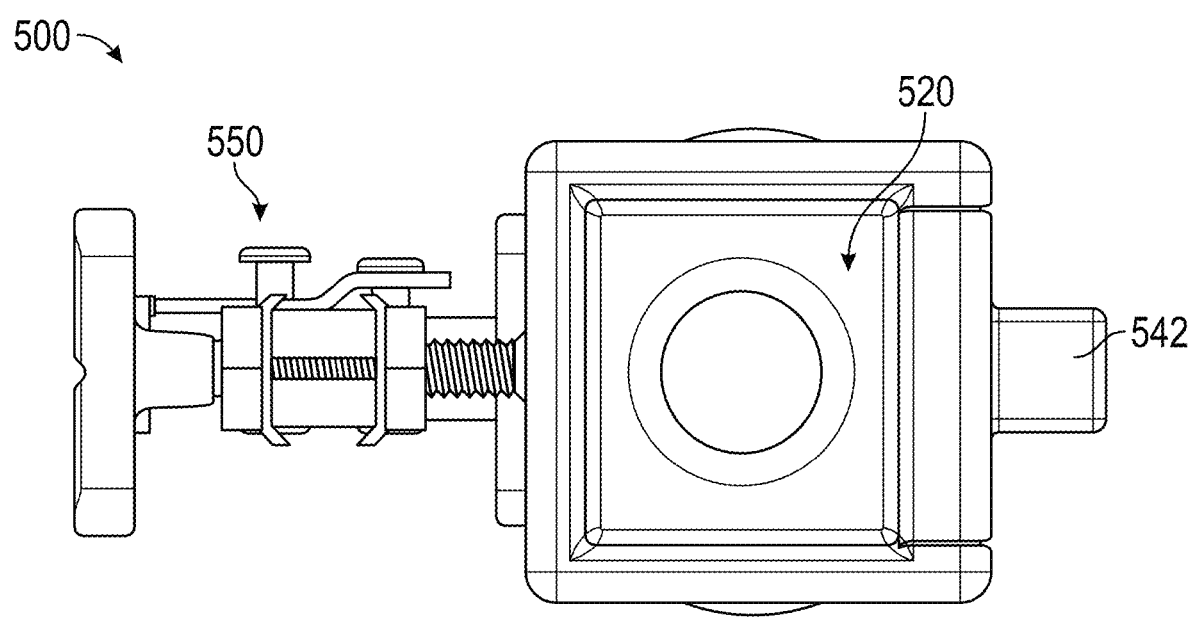

In the illustrative embodiment above, which uses the UR5 robotic arm 200 and the VCare® end effector 400, the mechanical interface 500 may be configured, for example, as shown in FIGS. 5A-5H, which show a closed/locked position. FIG. 5A is a front perspective view of an illustrative mechanical interface 500, showing the front and left sides thereof. FIG. 5B is a back perspective view of the mechanical interface of FIG. 5A, showing the back and right sides thereof. FIGS. 5C-5H show front, back, left side, right side, top, and bottom views of the mechanical interface of FIG. 5A, respectively. The top surface of mechanical interface 500 includes an extension/connector portion 510 configured to bolt to the robot arm 200 (or a sensor 600 attached to the robot arm 200, as described below). The bottom of mechanical interface 500 comprises an opening 520 through which the handle 406 of the uterine manipulator 400 is inserted into the mechanical interface 500. The left and/or right sides of mechanical interface 500 may have a slot 530 (e.g., an opening or window) therein so the user can see how deep the handle 406 is inserted. A quick release mechanism is preferably provided, whereby a front portion 540 of the mechanical interface 500 can be quickly detached from the rest of the mechanical interface 500, for example, by pushing against a protrusion 542 (e.g., in the direction of an arrow marked on front portion 540) and sliding front portion 540 until retaining tabs (not shown) align with recesses 544, allowing the front portion 540 to come off and release the handle of the manipulator. The back surface of mechanical interface 500 includes a latching mechanism 550 to releasably hold the handle 406 of the uterine manipulator 400 when the handle 406 is inserted into the mechanical interface 500 (see FIGS. 1A, 1B). Pushing latch 550 at position 552 urges the latch into a closed/locked position and pushes a screw 554 through an opening 556 in the back surface of the mechanical interface 500 so that screw 554 can abut/ engage the manipulator handle and hold it in place. A stopper 555 (see FIG. 8) made of rubber or other elastomeric material can be provided on the distal end of screw 554 to help secure the handle 406. Pushing latch 550 at position 558 can release/unlock the latch and enable screw 554 to retract from opening 556 (see FIG. 8, which illustrates an open/unlocked position).

Figure 6:
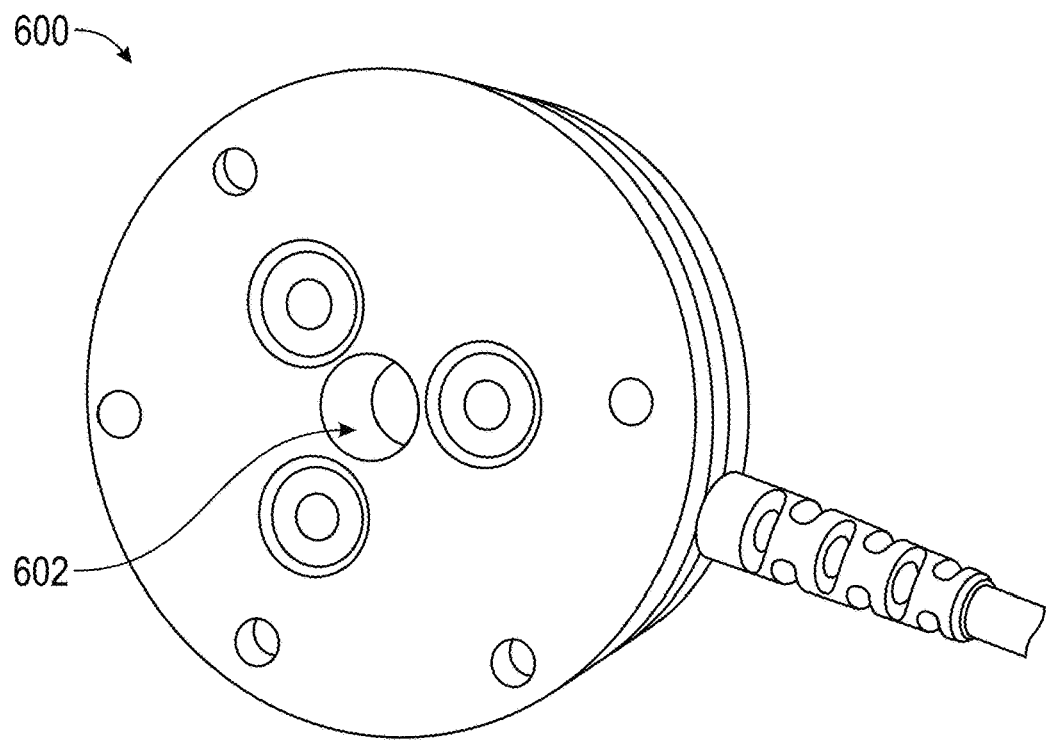
FIG. 6 is a perspective view of a sensor.
Figure 7:
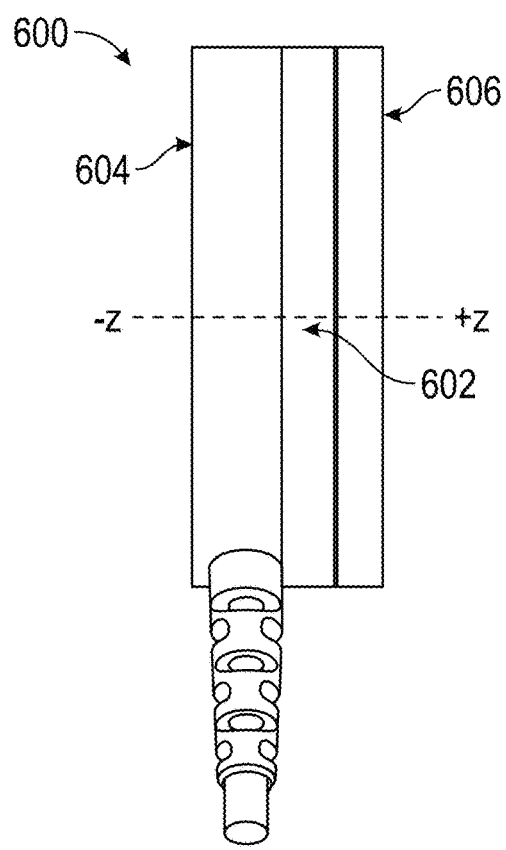
FIG. 7 is a side view diagram of the sensor of FIG. 6.

In some embodiments, a Force/Torque (F/T) sensor 600, such as the Mini40 from ATI Industrial Automation, Inc., may be provided on the distal end of arm 200. The Mini40 has a high strength, with EDM wire cut from high yield strength stainless steel. It also has a high signal-to-noise ratio, with silicon strain gages that provide a signal 75 times stronger than conventional foil gages. See, e.g., www.ati-ia.com/Products/ft/ft_models. aspx?id=Mini40. FIG. 6 is a perspective view of a Mini40-E Transducer, showing the tool side. FIG. 7 is a diagram showing a detailed side view of the Mini40-E Transducer, with the sensing reference frame origin 602, the mounting adapter plate 604 on the left, and the tool adapter plate 606 on the right (diagram taken from www.ati-ia.com/app_content/Documents/9230-05-1314.auto.pdf). In the Mini40, the mounting adapter 604 and tool adapter 606 may be made of aluminum or stainless steel, and the transducer may be hardened stainless steel. In other embodiments, a different type of F/T sensor 600, or individual force and/or torque sensors, may be used.

Figure 8:
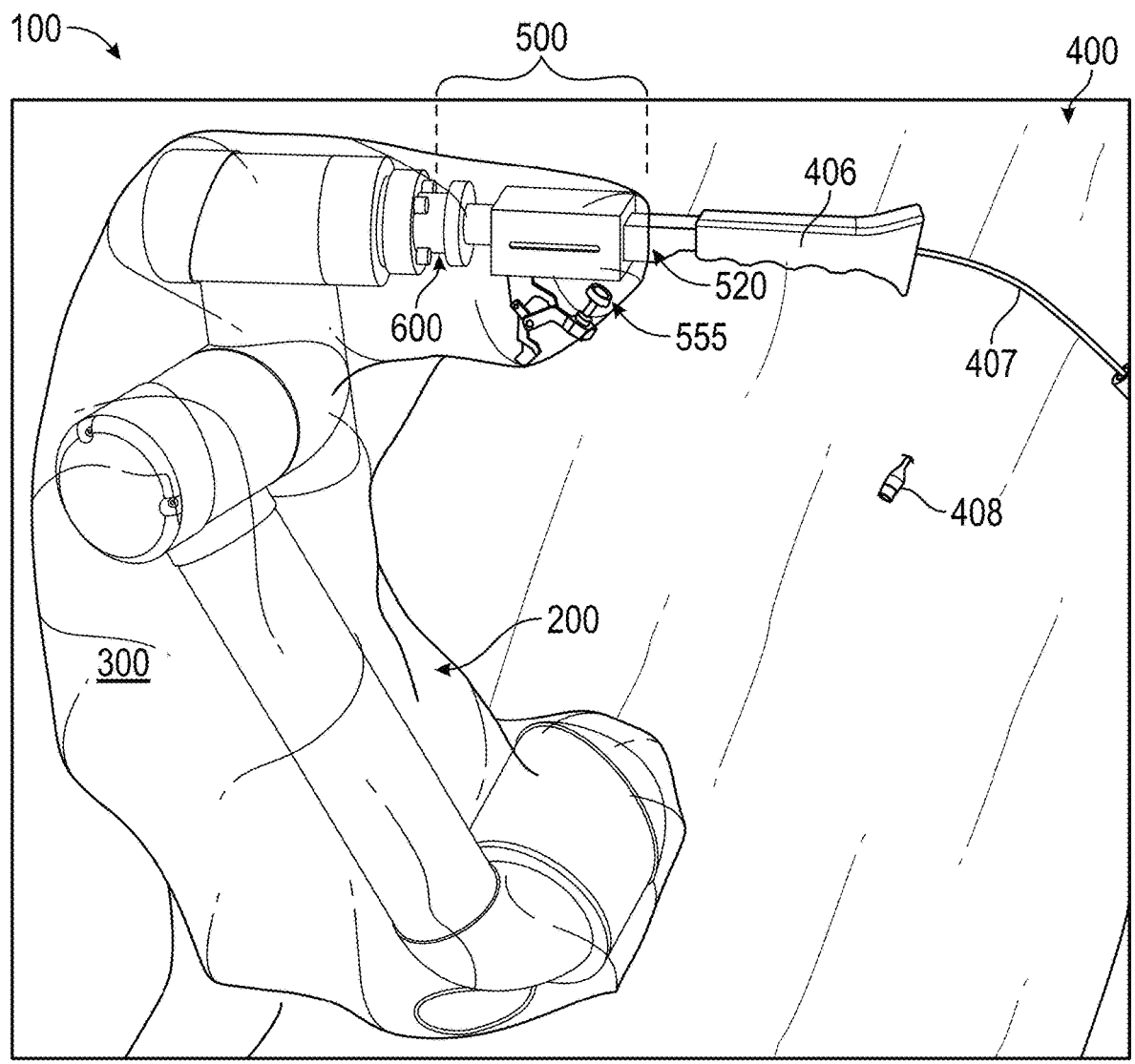
FIG. 8 is a perspective view of the uterine manipulation system of FIG. 1A, with the mechanical interface in an open position and the uterine manipulator detached therefrom.

FIG. 8 is a perspective view of the uterine manipulation system of FIG. 1A, with the mechanical interface 500 unlatched and the VCare® uterine manipulator 400 detached therefrom. As shown in FIG. 8, a sensor 600 such as the Mini40 may be attached to a distal end of the UR5 arm 200, in which case the mechanical interface 500 may be bolted to the sensor 600 instead of directly to the arm 200. A rubber stopper 555 may be attached to the end of the screw 554 on the mechanical interface latch 550. A disposable sterile drape 300 (e.g., a transparent plastic drape) may be provided, which as shown in FIG. 8 can cover the arm 200, the sensor 600, and at least a portion of the mechanical interface 500 (e.g., to maintain a sterile field between the patient and the robot). The handle 406 of the uterine manipulator 400 can be inserted into the opening 520 on mechanical interface 500, and the mechanical interface latch 550 can be closed (e.g., such that the rubber stopper 555 fits into a groove on the handle 406).

Figure 9:
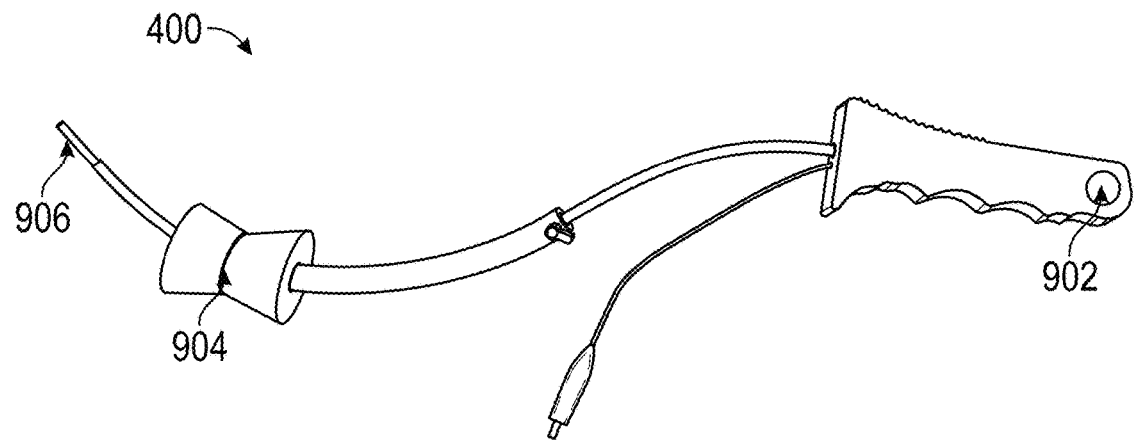
FIG. 9 is a side view of the uterine manipulator of FIG. 4, illustrating reference points (tip, fulcrum, handle) for kinematics.
Figure 10:
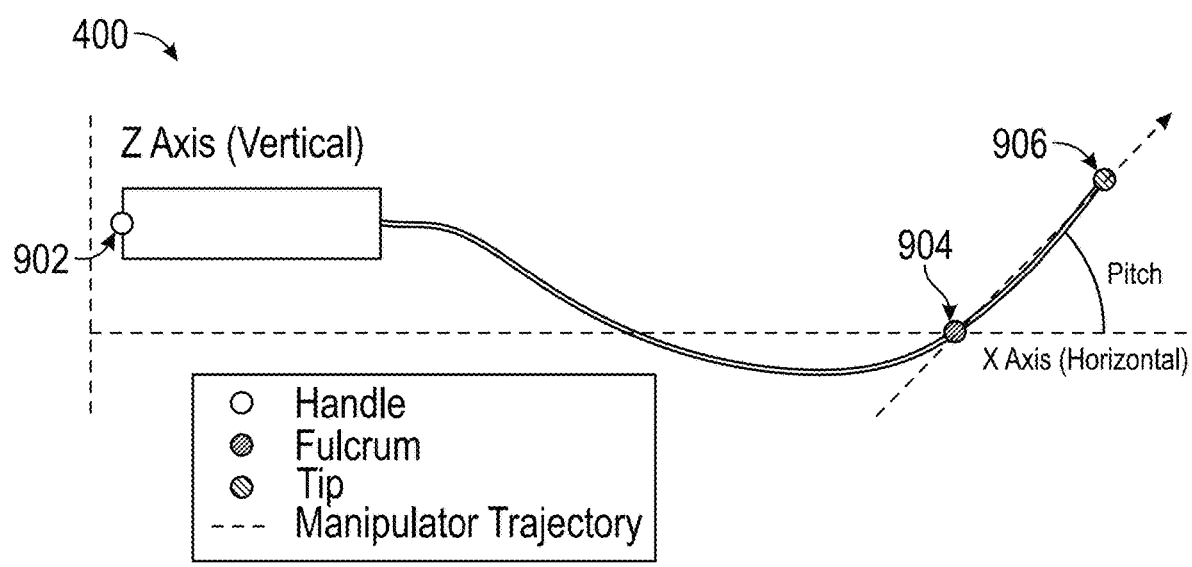
FIG. 10 is a side view diagram of the uterine manipulator of FIG. 9, in a baseline position, illustrating pitch.
Figure 11:
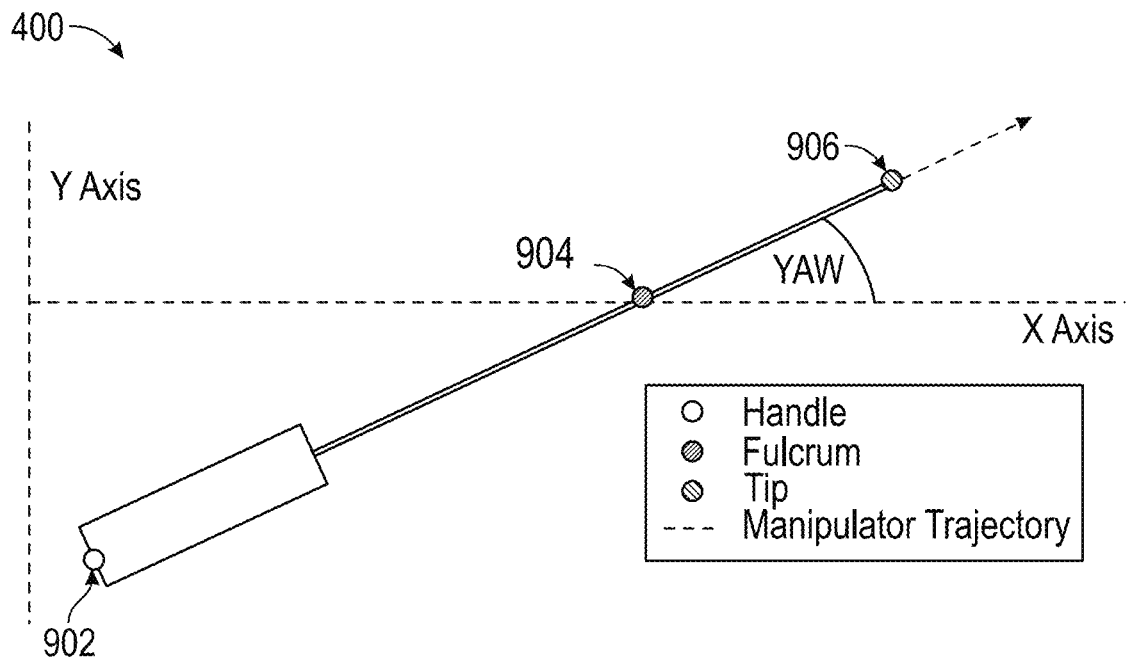
FIG. 11 is a top view diagram of the uterine manipulator of FIG. 9, in the baseline position, illustrating yaw.
Figure 12:
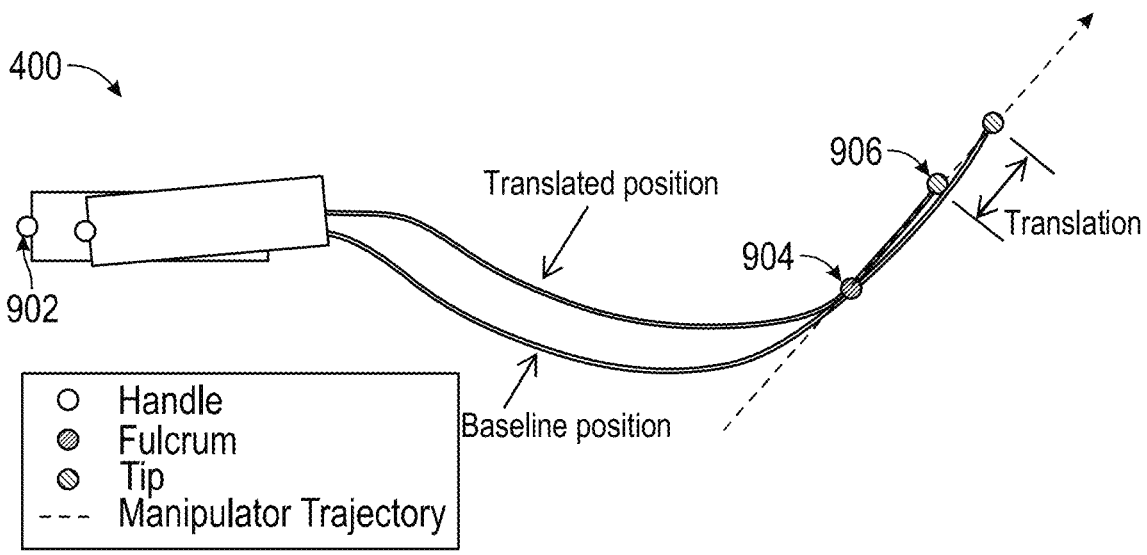
FIG. 12 is a side view diagram of the uterine manipulator of FIG. 9, illustrating a translation from the baseline position to a translated position.

FIGS. 9-12 illustrate movement of the uterine manipulator 400, according to some embodiments of the invention. FIG. 9 is a side view of the uterine manipulator of FIG. 4, indicating reference points (handle 902, fulcrum 904, tip 906) for kinematics, which reference points are repeated in FIGS. 10-12. The distance from the fulcrum to the tip is dependent on the individual patient. This patient-specific distance is measured using the numbered marks on the VCare®. The number corresponding to the locking position may be entered into the kinematics software via the control console at robot setup following VCare® insertion (see, e.g., FIG. 15 "Fulcrum Position (cm)"). FIG. 10 is a side view diagram of the uterine manipulator 400 in a baseline position, illustrating pitch. In the baseline position, the uterine manipulator is held in a vertical plane with the handle 902 parallel to the floor and the tip 906 pointed upward. The baseline/starting position (0, 0, 0) may be hard coded as a point in 3-D space. FIG. 11 is a top view diagram of the uterine manipulator 400 in the baseline position, illustrating yaw. FIG. 12 is a side view diagram of the uterine manipulator 400, illustrating a representative translation from the baseline position to a translated position. Joystick movement at the console determines the motion of the tip 906.

Arm Motion

FIGS. 17A-17D are side, front, top, and perspective schematic views, respectively of a robotic uterine manipulation system 100 according to various embodiments of the invention, including a mobile cart 700, arm 200, and mechanical interface 500 (end effector 400 not attached/shown). As shown, arm 200 is configured to provide +/− translation in the X, Y, and Z directions, as well as rotation in the clockwise and counterclockwise directions.

In some embodiments, the arm can manually position the uterine manipulator with a starting pitch of +0/−30 degrees from the baseline position. The arm can also be controlled by a programmable controller. In some embodiments, the arm can position the uterine manipulator tip at least +50 degrees and −40 degrees of pitch from the starting positions defined above. Uterine manipulator tip pitch is measured from fulcrum to tip. In some embodiments, the arm can position the uterine manipulator tip at least +45 degrees and −45 degrees of yaw from the starting positions defined above. In some embodiments, the arm can translate the uterine manipulator tip forward 8 cm from the starting positions defined above. Translation is along the line defined between fulcrum and tip. In some embodiments, the arm can position the uterine manipulator at the extremes of pitch, yaw, and translation simultaneously. In some embodiments, the arm can apply 5 pounds of force in the forward translation direction described above. In some embodiments, the uterine manipulator handle can move no more than 1 cm when a force of 5 pounds is applied at the uterine manipulator tip in any primary direction. This accounts for arm motion and handle/receptacle interface slope.

Cart

Figure 18A:
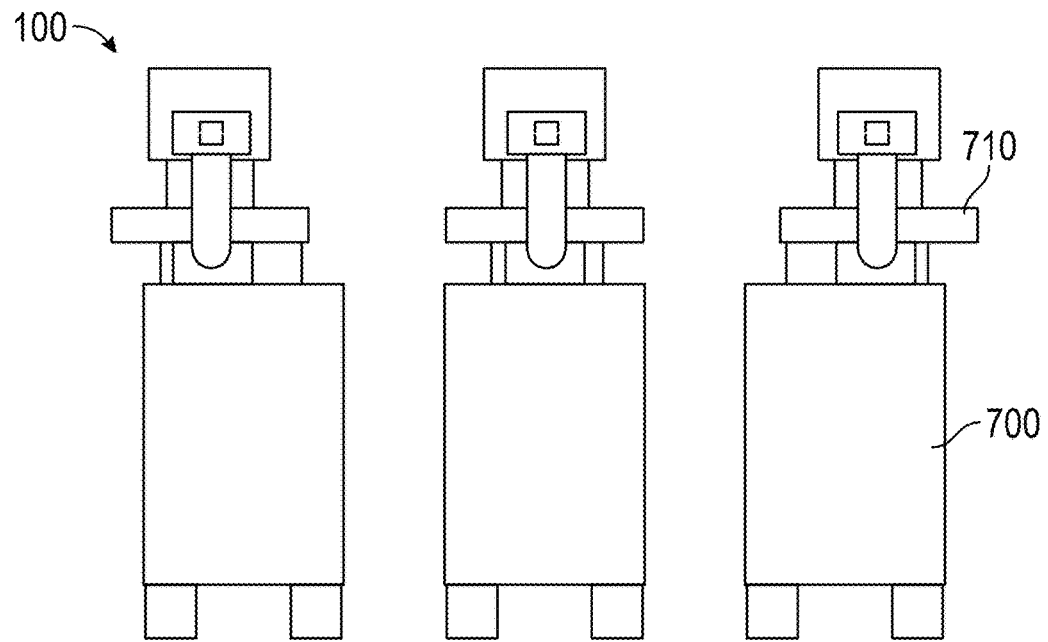
FIG. 18A-18C are front and side views of a robotic uterine manipulation system as depicted in FIGS. 17A-17D, showing an illustrative cart with setup positioning system.
Figure 18B:
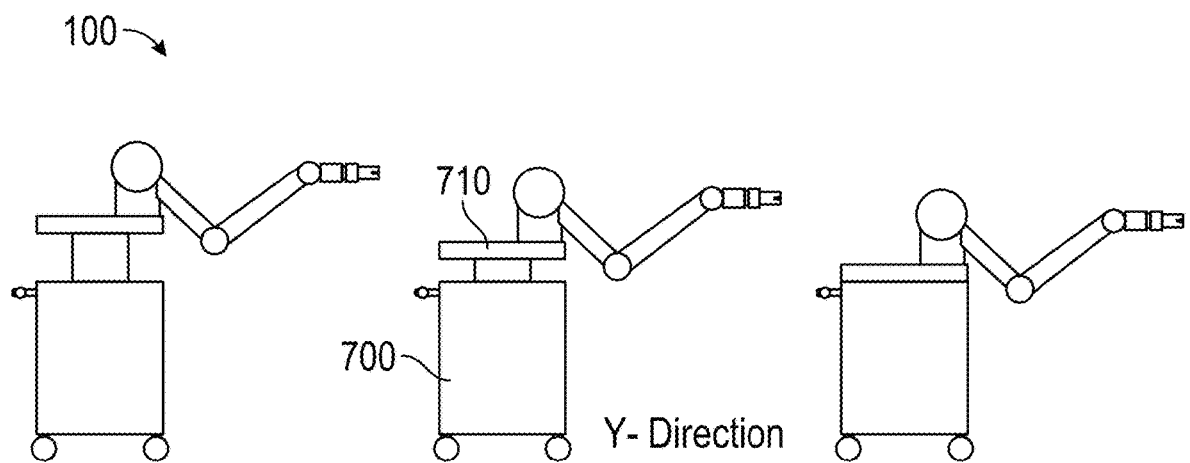
Figure 18C:
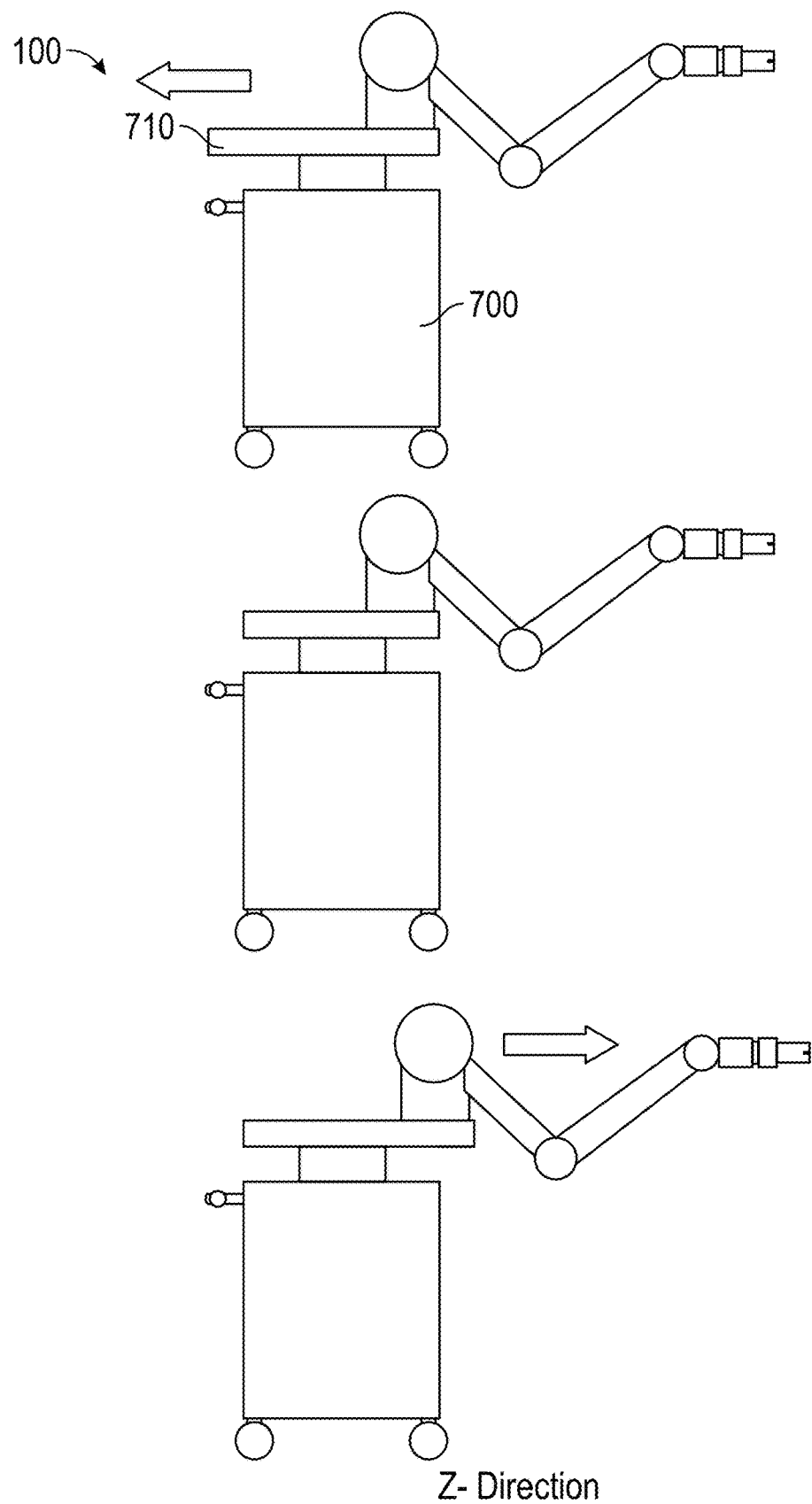

FIG. 18A is a front view and FIGS. 18B and 18C are side views of a robotic uterine manipulation system 100 as depicted in FIGS. 17A-17D according to various embodiments of the invention. As shown in FIGS. 18A-18C, in some embodiments, cart 700 can include a setup positioning system 710 (e.g., comprising a substantially horizontal moveable platform/base) to which arm 200 may be releasably or permanently secured. Positioning system 710 may be configured to provide, for example, +/− translation in the X, Y, and/or Z directions. Setup positioning system 710 can be used for initial positioning, prior to finer positioning of arm 200 (and mechanical interface 500, end effector 400 attached thereto) for anatomical manipulation.

In some embodiments, the cart can position the uterine manipulator at the baseline position in a height range of about 39 inches to about 48 inches (e.g., corresponding to 5th percentile and 95th percentile elbow heights). The cart can remain stationary when the brake is applied and up to 22 pounds of force is applied to the top edge of the cart. All wheels of the cart can remain fully in contact with the floor when 22 pounds of force is applied to the arm at the baseline arm position and wheels are locked. Immobilization at 22 pounds of force was deemed sufficient stability for safe use in uterine manipulation cases; however, the cart may be configured to withstand other force limits (higher or lower)

for other applications. The robot can position the uterine manipulator in a baseline position with an operating table tilt between 0 degrees and −30 degrees reverse Trendelenburg. The robot can be powered from universal 100-240 VAC 50-60 Hz. The robot can monitor force and torque of the arm for independent safety override functionality. Safety monitoring and intervention can be independent from the robot positioning system. The robot can include an emergency stop capability.

Mechanical Interface

Figure 19A:
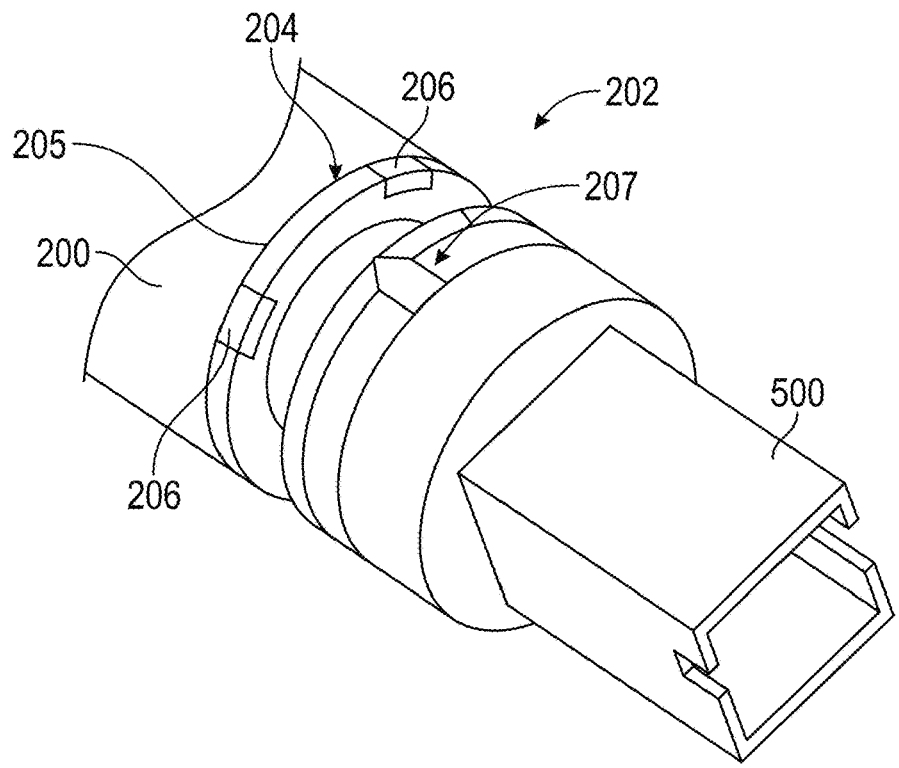
FIGS. 19A and 19B are perspective views showing illustrative visual indicators of an acceptable range for a start position, according to various embodiments of the invention.
Figure 19B:
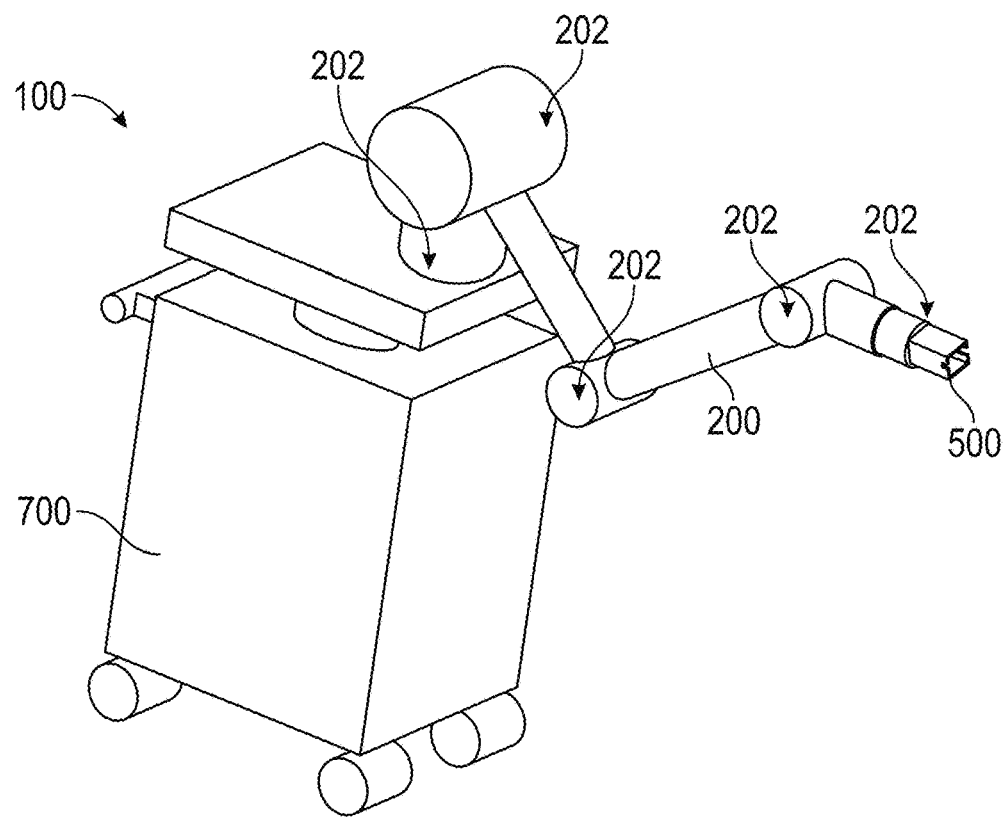

FIG. 19A is a detailed view of illustrative markings 202 at the distal end of arm 200, which connects to mechanical interface 500. Markings 202 can function generally to provide a visual indicator of an acceptable setup range for a joint position. For example, a range indicator strip 204 can be provided on one side of a given joint. A central portion 205 of range indicator strip 204 can indicate an acceptable setup range. Optional end portions 206 of range indicator strip 204 can mark outer limits of the acceptable setup range. A range position arrow 207 can be provided on the other side of the joint to indicate whether the position is within the acceptable range. When the arrow 207 is within the central portion 205 of range indicator strip 204, the user may be assured of an acceptable start position. As shown schematically in FIG. 19B, in some embodiments, visual indicators/markings 202 may be provided on all joints. In other embodiments, visual indicators/markings 202 may be provided on only a subset of joints.

In some embodiments, the arm can maintain connection with the uterine manipulator via the mechanical interface when, for example, about 5 pounds of force is applied at the tip of the uterine manipulator in any primary direction. In some embodiments, the mechanical interface can include a "quick-release" mechanism that will allow the uterine manipulator to be released, for example, in under 5 seconds without moving the robot arm or cart.

Console

Figure 20A:
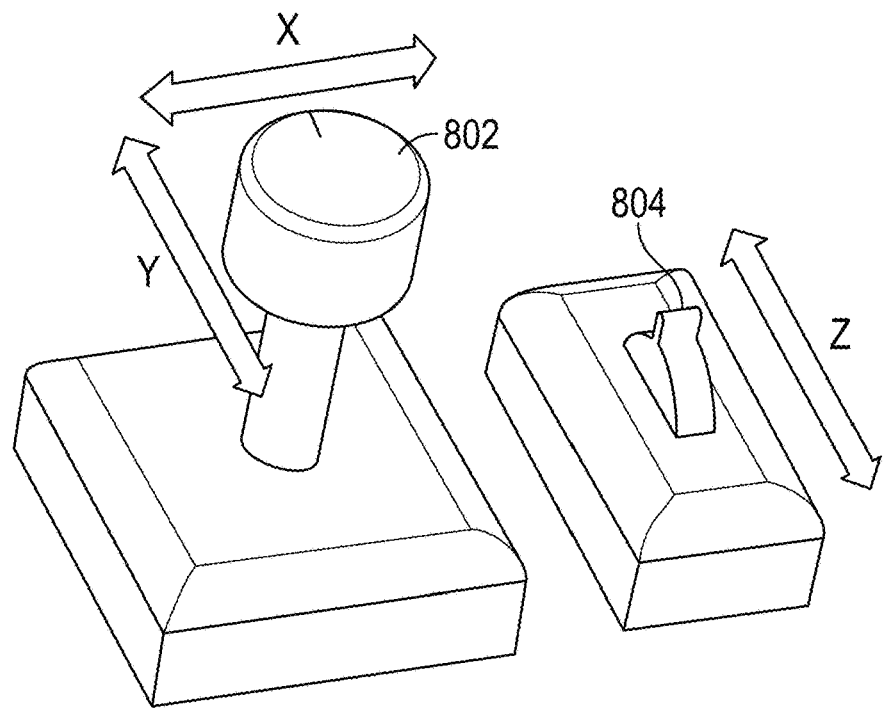
FIGS. 20A and 20B are perspective and top views, respectively, of illustrative user controls on a console of a robotic uterine manipulation system according to various embodiments of the invention.
Figure 20B:
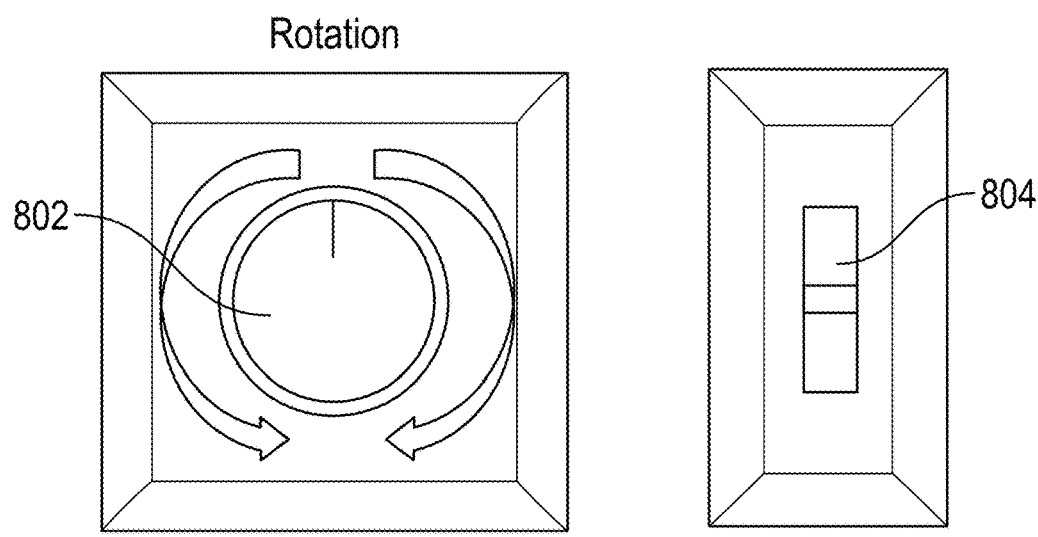
Figure 21A:
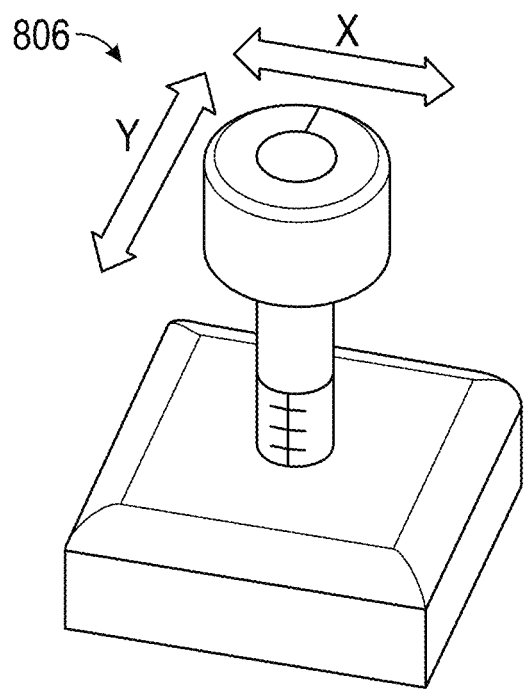
FIGS. 21A-21C are perspective, top, and side views, respectively, of other illustrative user controls on a console of a robotic uterine manipulation system according to various embodiments of the invention.
Figure 21B:
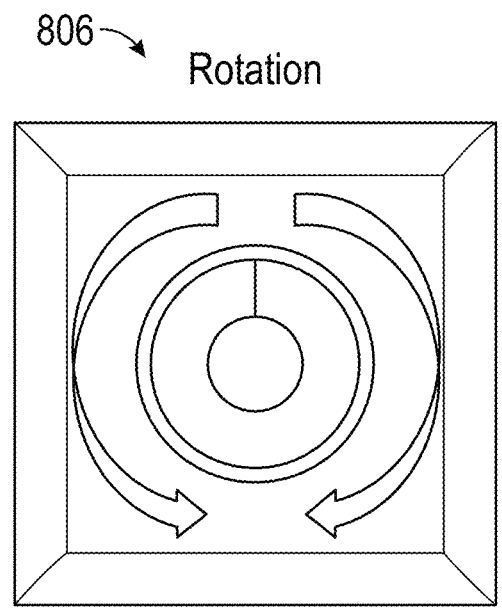
Figure 21C:
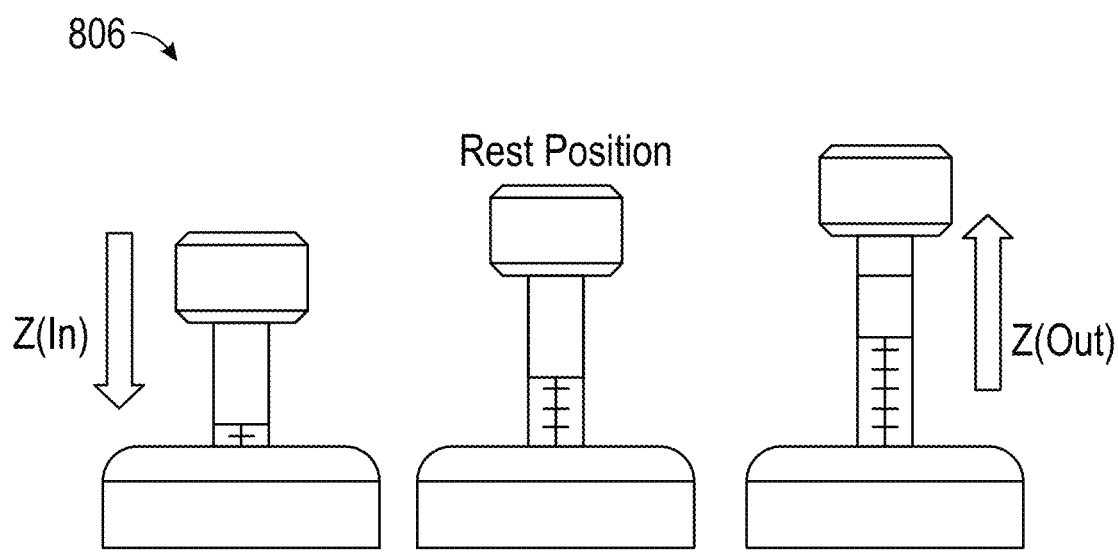
Figure 22:
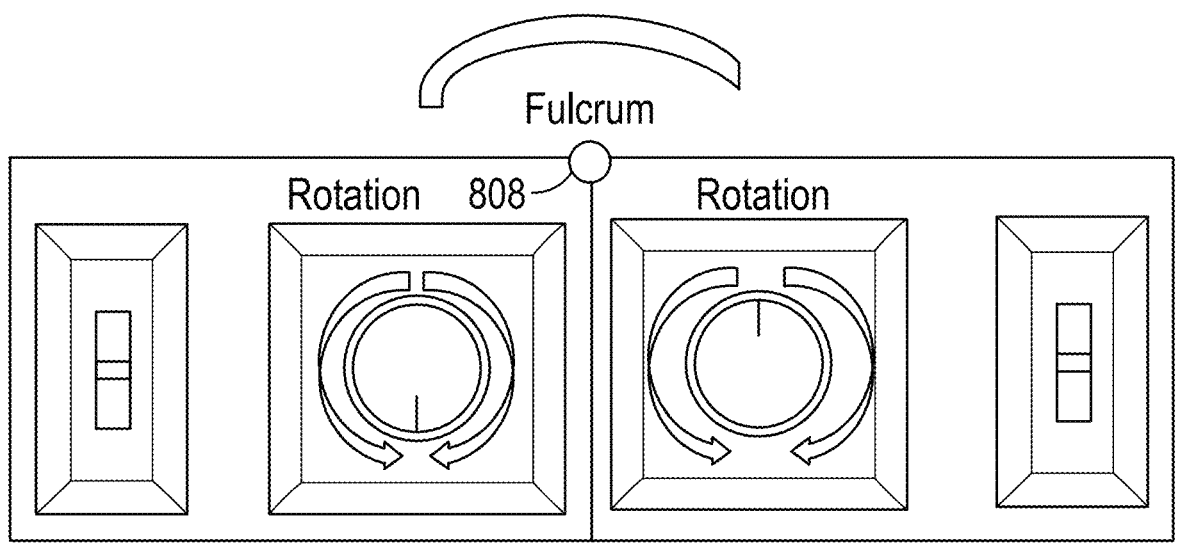
FIG. 22 is a top view showing moveable user controls on a console of a robotic uterine manipulation system according to various embodiments of the invention.
Figure 23:
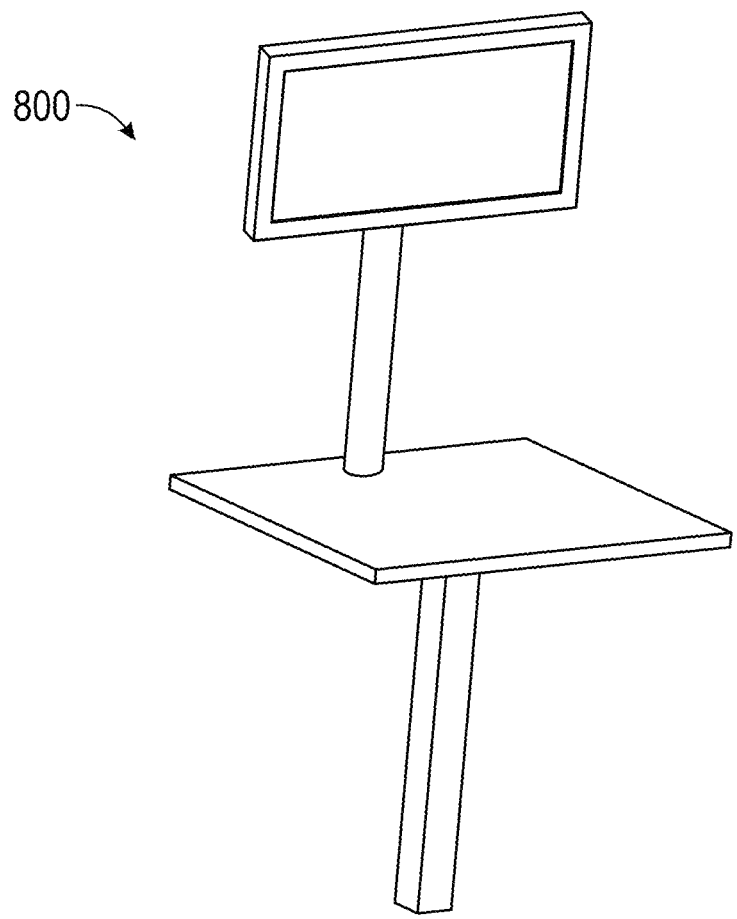
FIG. 23 is a perspective schematic view of a console of a robotic uterine manipulation system according to various embodiments of the invention.
Figure 24:
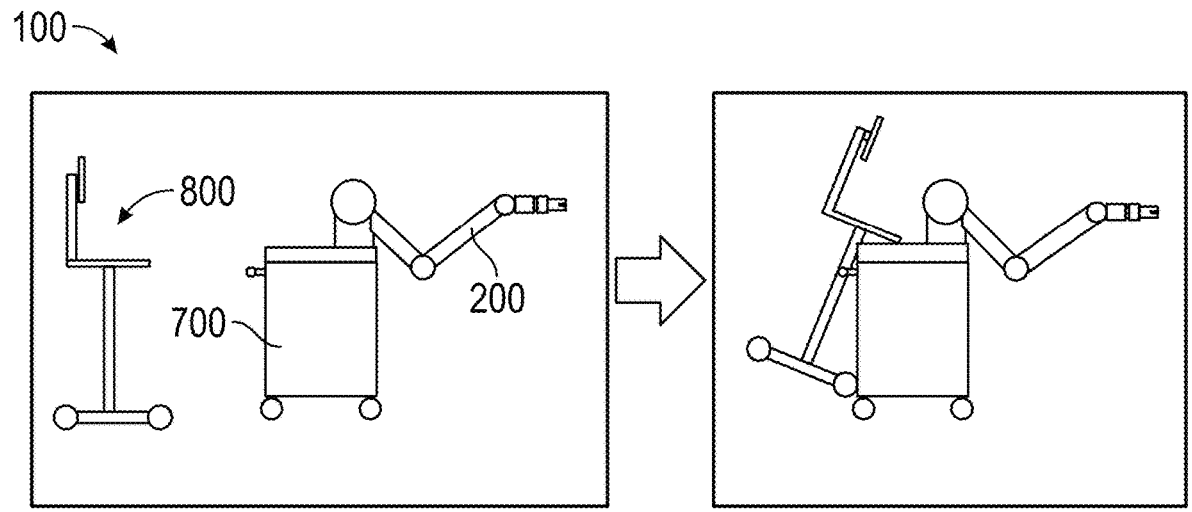
FIG. 24 is a side schematic view showing transport of a robotic uterine manipulation system according to various embodiments of the invention.

FIGS. 20A and 20B are perspective and top views, respectively, of illustrative user controls on a console 800, which is part of a robotic uterine manipulation system 100 according to various embodiments of the invention. A joystick 802 may provide translation in the X and Y directions, as well as clockwise/counterclockwise rotation, while a switch or roller 804 may provide translation in the Z direction. In other embodiments, different user controls may be provided to control the robot degrees of freedom. For example, a joystick 806 may be provided, which provides translation in the X and Y direction as shown in FIG. 21A, rotation in either direction as shown in FIG. 21B, and translation in the Z direction as shown in FIG. 21C. In some embodiments, the user controls may be movable, so that they can have either a left or a right side orientation on the control panel. For example, as shown in FIG. 22, user controls as shown in FIG. 20B may be rotated about a fulcrum 808 from a left to a right orientation, and vice versa. FIG. 23 is a schematic of a control console 800, according to some embodiments. Preferably, the console provides a user interface having one or more control surfaces/mechanisms, video capability, and/or touch screen or other capability. Cart 700 and console 800 are preferably configured to be easily transported (e.g., to different areas of a hospital by a single person). FIG. 24 is a side schematic view of an illustrative system transport/gross movement solution for a robotic uterine manipulation system 100 according to various embodiments of the invention.

Figure 25:
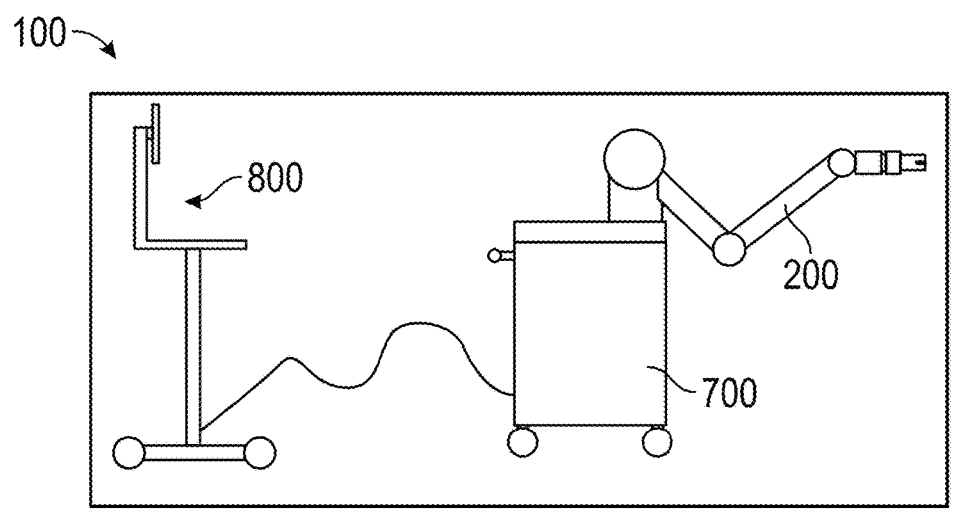
FIG. 25 is a side schematic view of an illustrative wired connection for a console and a robot of a robotic uterine manipulation system according to various embodiments of the invention.

In some embodiments, the robot can receive control inputs from the user via a wired remote console. The wired connection can be, for example, at least 15 feet (e.g., to provide sufficient room for a surgeon and/or a surgical robot), although other lengths can be used. FIG. 25 is side schematic view of an illustrative cable connection/cable management solution for a robotic uterine manipulation system 100 according to various embodiments of the invention. Preferably, cables can be connected/disconnected (e.g., for transportation/shipping, storage, service, etc.) and can be stowed effectively when not in use. The console can control the position of the arm. The console can provide a user interface for the user to input configuration parameters (e.g., sounding depth, boundaries, speed). The console can include a mechanism (such as a button) that can disable movement control of the arm from the joystick and user interface when actuated. This is to ensure safety during critical times of surgery such as cauterization. This ensures that user and system errors cannot cause spurious arm movement. The console can include a user interface that can provide visual feedback (e.g., a warning message and/or light). The console can also include a user interface that can provide audible feedback (e.g., a beep or other warning sound). The audible feedback can indicate motion and can function, for example, as a movement alarm and/or speed alarm. The volume of the alarm may be programmable, and the pitch/tone/pattern may provide audible indication, for example, of both movement and speed. The user controls and user experience are preferably customizable. For example, force levels, physical positioning of controls, and/or alarm levels may be customized according to surgeon (or other user) preference. In some embodiments, a back off mode may be provided, whereby in the event of reaching a force or geometry limit, the user can bring the system back to safe movement or fix manually. In some embodiments, a stop axis indicator may be provided, whereby the system can visibly indicate which axis/control is locked up/at maximum. Such visualization may include text and/or diagram, preferably both.

Figure 26:
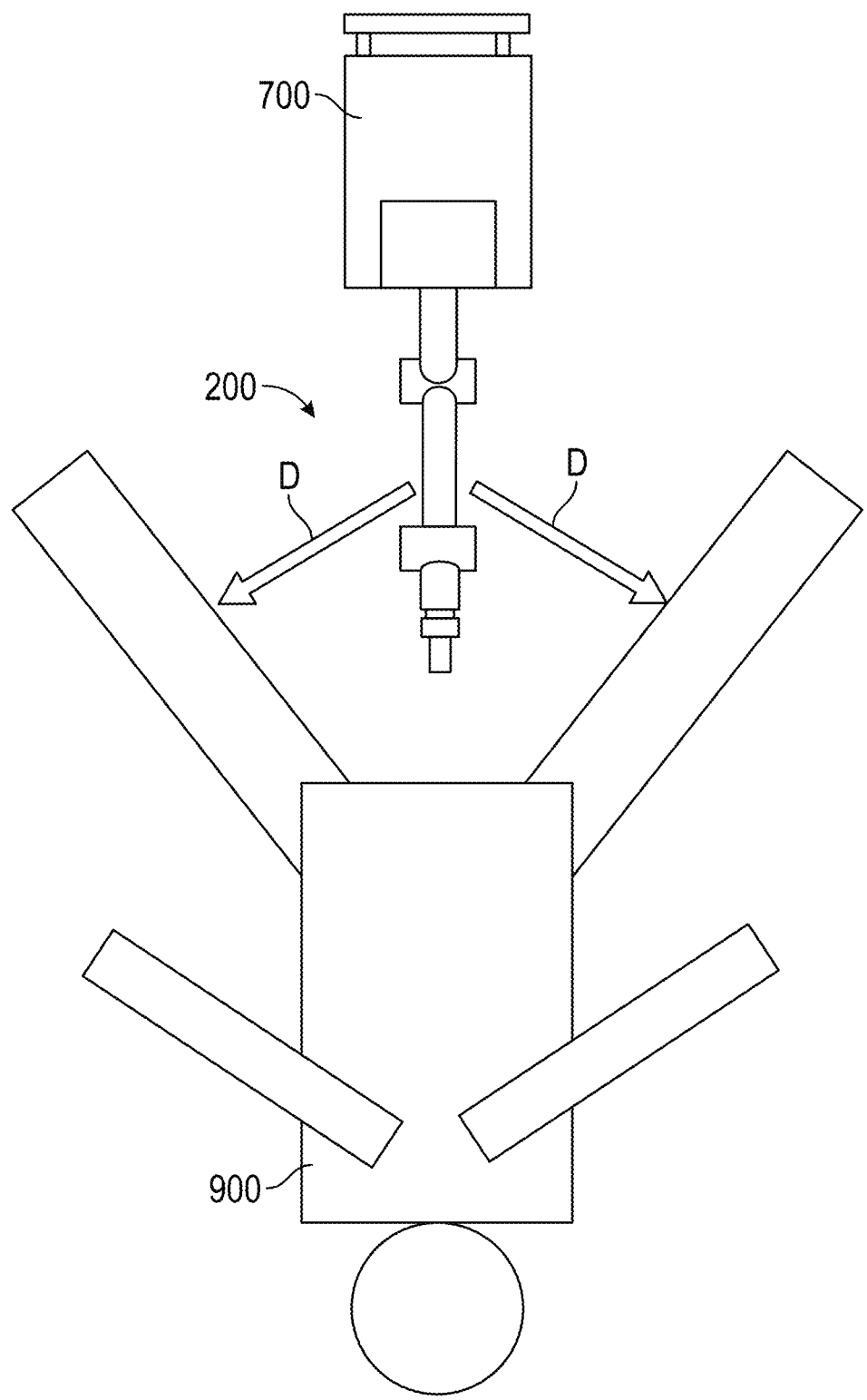
FIG. 26 is a top schematic view of a robotic uterine manipulation system according to various embodiments of the invention, showing symmetric insertion into a patient.

Preferably, a robotic uterine manipulation system 100 according to embodiments of the invention is configured for symmetric insertion, and can provide equal range of motion in either direction (+/−) along all axes. For example, as shown in FIG. 26 which depicts a schematic robot (cart 700 and arm 200) and patient 900, in some embodiments, distances D may be substantially equal in all ranges of motion.

Sterility

In some embodiments, the arm can meet the above-described motion requirements while covered by a sterile drape. The drape can provide a sterile boundary between the arm and the uterine manipulator, ensuring that sterility of the uterine manipulator is maintained during docking. As used herein, docking refers to the act of mating the uterine manipulator into the robot arm mechanical interface. The console can also perform its intended functions while covered by a sterile drape. The robot can be cleaned with standard hospital cleaning agents. The console can be cleaned with standard hospital cleaning agents.

Standards Compliance

In some embodiments, the system can include Instructions for Use (IFU). All labeling conforms to the requirements described in 21 CFR 801. The system labeling complies with the U.S. Food and Drug Administration's Unique Device Identification requirements. The system preferably meets the requirements of IEC 60601-1:2005 (Medical Electrical Equipment—Part 1: General Requirements for Basic Safety and Essential Performance).

System Software

Embodiments of the present invention also provide software for operating the robotic anatomical manipulation systems. The software may include, for example, existing robotic arm software (e.g., UR5 Software), a combination of existing robotic arm software and custom-built system software (e.g., UR5 Software+LabVIEW System), and embedded software (e.g., Embedded Safety System), as described further below.

Positioning and Motion

The software can place the arm in Freedrive Mode, where the user can manually move each joint of the arm to a desired position. The software can place the arm in Manipulation Mode, where the user can control the positioning of the arm via the joystick. In Freedrive Mode (UR5 Software), the software can maintain the new position of the arm once the user manually moves it. During the transition to Manipulation Mode from Freedrive Mode, the software can maintain the arm in its manually set position. In Manipulation Mode (UR5 Software+LabVIEW System), the robot arm does not respond to external force that does not exceed robot arm maximum load (i.e., it can maintain its position unless commanded via user input through joystick or GUI). The software can stop arm motion and maintain the arm's position when the user removes input (through joystick or GUI). The software can record a position of the arm and allow the user to, with as few as a single input, cause the arm to automatically return to that position while in Manipulation Mode. One such position is the Home Position. The Home Position refers to the initial position of the arm after using Freedrive to mate the arm to the uterine manipulator (this position should generally have a yaw of 0). When force and/or torque readings in a certain direction of movement exceed a predetermined LabVIEW Force or Torque Threshold during motion in Manipulation Mode, the software can prevent continued motion of the arm in that direction. In some embodiments, for use in uterine manipulation, it was determined that a preferred LabVIEW Force Threshold was at or about 10 lbf (pounds-force) and a preferred LabVIEW Torque Threshold was at or about 70 in-lbs (inch-pounds-force). In other embodiments, different LabVIEW Torque and/or Force Threshold values may be set. When an upward pitch input is specified by the user, the software moves the arm to perform the upward pitch. When a downward pitch input is specified by the user, the software moves the arm to perform the downward pitch. When a leftward yaw input is specified by the user, the software moves the arm to perform the leftward yaw. When a rightward yaw input is specified by the user, the software moves the arm to perform the rightward yaw. When a forward translation input is specified by the user, the software moves the arm to perform the forward translation. When a backward translation input is specified by the user, the software moves the arm to perform the backward translation.

Safety

The embedded software (Embedded Safety System) can acquire six channels of force and torque corresponding to: Fx, Fy, Fz, Tx, Ty, and Tz. The embedded software can acquire force and torque values at least 100 times per second. The embedded software controller can monitor force and generate a digital signal to disable all or a subset of arm motion when the force reading meets or exceeds a predetermined Embedded System Force Threshold. The embedded software controller can also monitor torque and generate a digital signal to disable all or a subset of arm motion when the torque reading meets or exceeds a predetermined Embedded System Torque Threshold. Torque calculations assume force is applied at the farthest tip of the uterine manipulator. In some embodiments, for use in uterine manipulation, it was determined that a preferred Embedded System Force Threshold was at or about 12 lbf and a preferred Embedded System Torque Threshold was at or about 90 in-lbs. In other embodiments, different Embedded System Force and/or Torque Threshold values may be set. The embedded software controller can allow the user to disable motion control by activating the 'Safeguard Stop' function of the robot arm. The disabling of motion control by the embedded software controller can prevent/cancel the Freedrive capability of the arm, and can be controlled, for example, via an enable/disable button on the console cart.

User Interface

Figure 15:
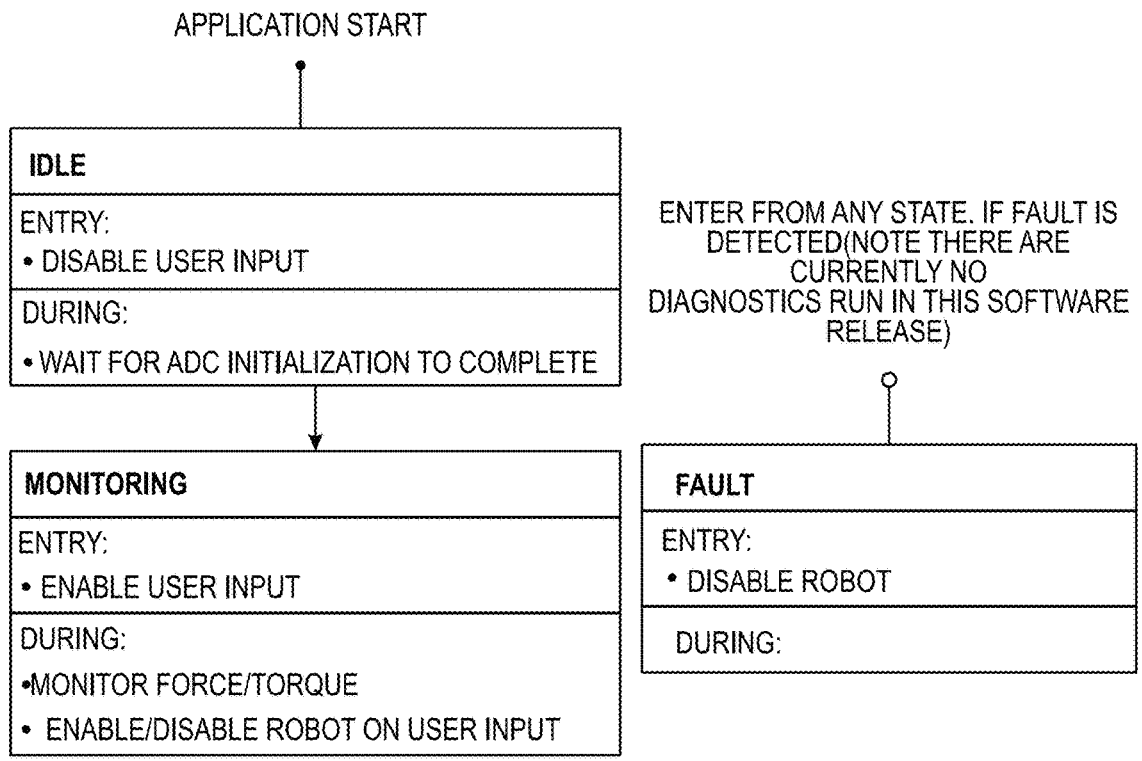
FIG. 15 is a diagram of a top level item finite state machine.
Figure 16:
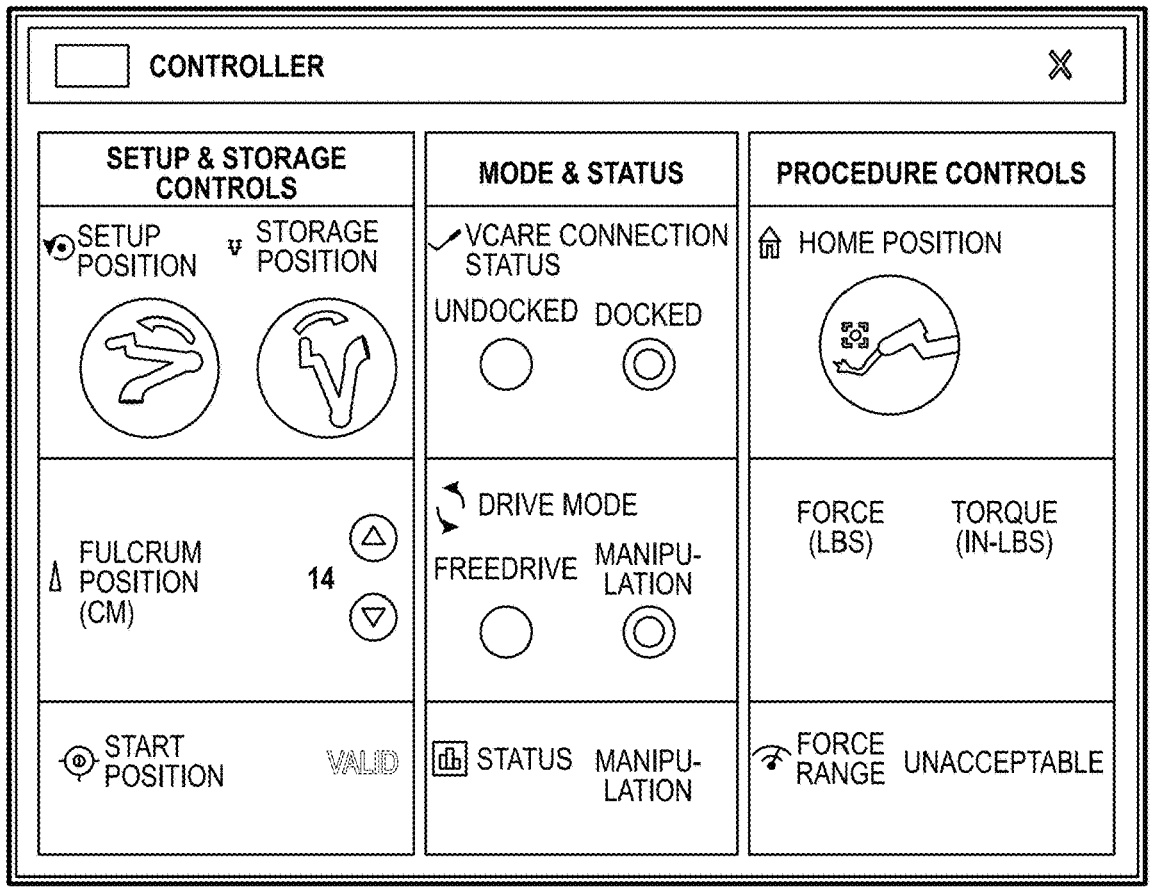
FIG. 16 is a diagram of a graphical user interface, according to various embodiments of the invention.
Figure 17A:
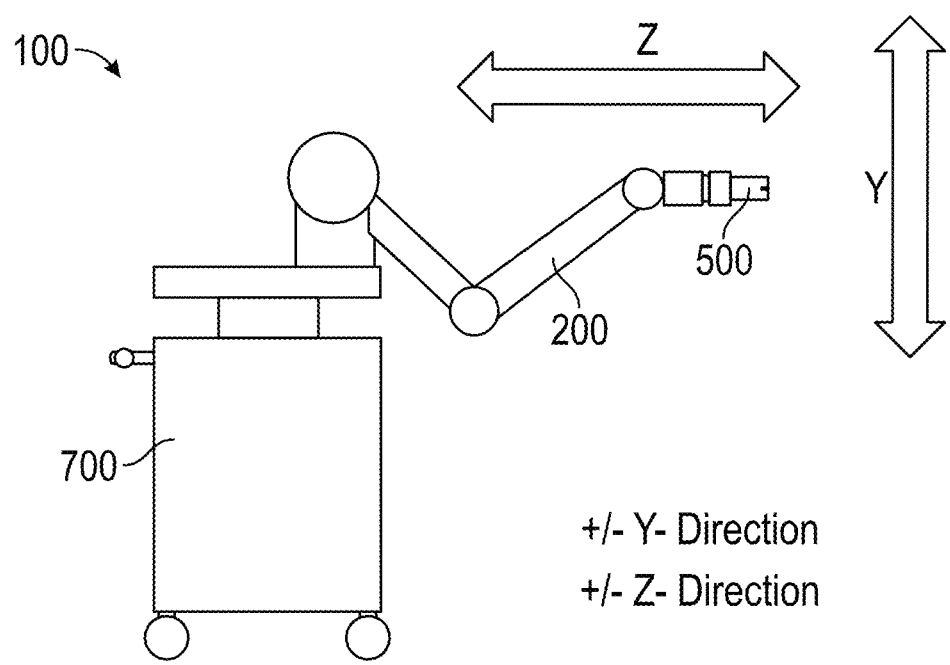
FIGS. 17A-17D are side, front, top, and perspective schematic views, respectively of a robotic uterine manipulation system according to various embodiments of the invention, showing illustrative degrees of freedom for the arm.
Figure 17B:
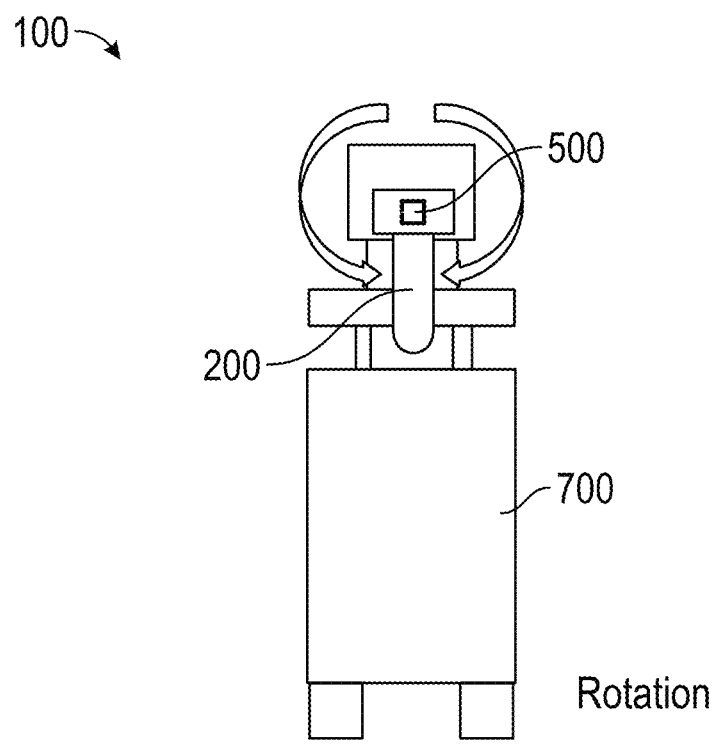
Figure 17C:
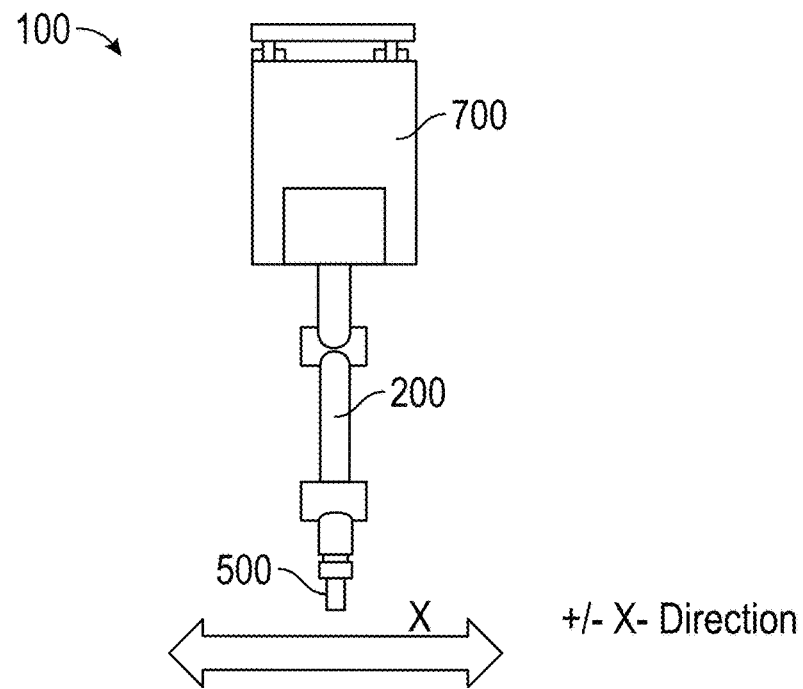
Figure 17D:
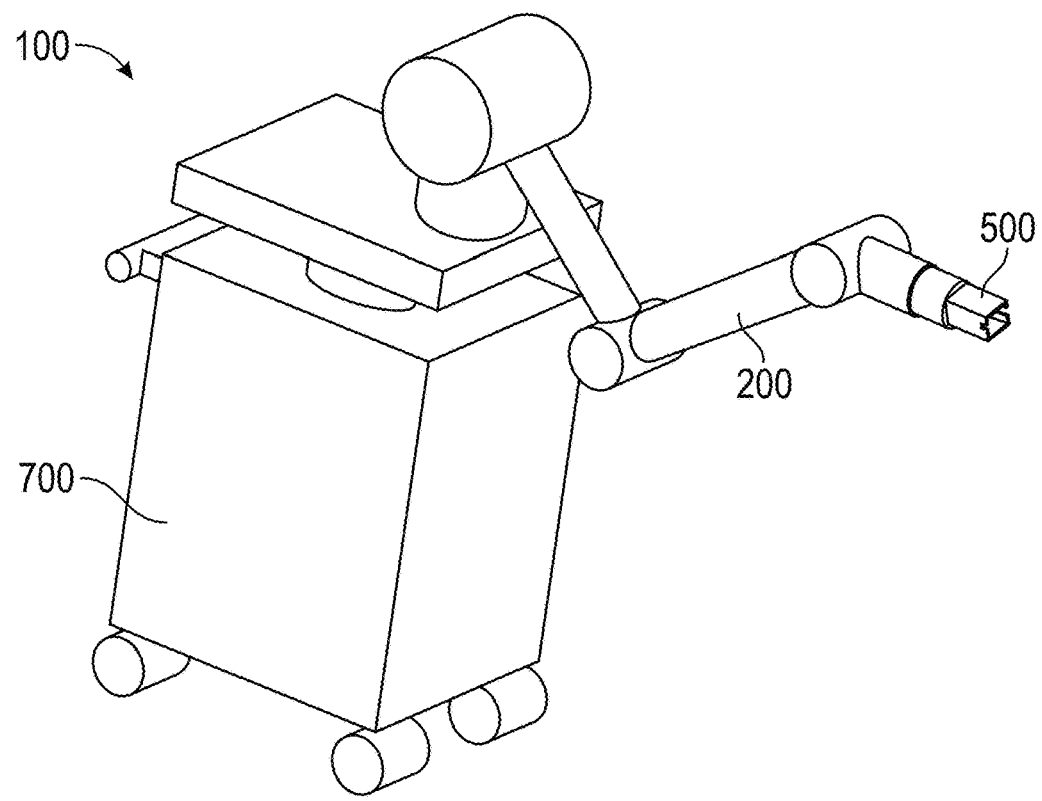

The software (LabVIEW System) can generate a Graphical User Interface (GUI) to provide touchscreen controls and display feedback (e.g., as shown in FIG. 15). The GUI can provide the user the ability to toggle between Freedrive Mode and Manipulation Mode. The GUI can provide feedback indicating the state of the robot (e.g., Manipulation Mode or Freedrive Mode). The GUI can provide feedback to the user indicating whether the starting position (Home Position) is valid or invalid. A valid home position means that the arm can achieve the full desired range of motion from that position. The GUI can display the measured real-time force and/or torque values to the user, such that an operator can be advised when force or torque thresholds are being approached. These can be displayed on the user interface, for example, as a single resultant force value and/or a single resultant torque value. The GUI can provide visual feedback when either the LabVIEW Force or Torque Threshold is approached or reached. The GUI can provide audible feedback when either the LabVIEW Force or Torque Threshold is approached or reached. The GUI can allow the user to set the fulcrum position prior to entering Manipulation Mode.

Software System Architecture

Overview

Embodiments of the present invention provide the following software components: UR5 Robot and Control System; LabVIEW Control System; Embedded Safety System.

The UR5 Robot and Control System is an off-the-shelf closed-loop robot comprising a motorized arm, single board computer control system, user interface touch panel, and supervisory safety processor. The UR5 Robot and Control System interface with external applications through a TCP/IP interface and Digital I/O lines. The software running on the UR5 single board computer, safety processor, and touch panel are considered "SOUP" units (software of unknown provenance) that interface with the remaining software architecture via the TCP/IP and Digital I/O interface.

The LabVIEW Control System is a custom LabVIEW development environment running on a Windows PC. In various embodiments, the LabVIEW application provides one or more of the following functionalities: captures operator motion control from the joystick/mouse; provides a touchscreen user interface for system control; allows the user to activate and deactivate Freedrive Mode; calculates kinematics for robot motion and sends commands to the robot; monitors force and/or torque feedback from the end effector; sends a stop signal to the robot if the force or torque thresholds are reached or exceeded.

The Embedded Safety System (embedded system) is custom firmware running on an Atmel® XMEGA® C3 platform, which contains a 16-bit mega microcontroller (e.g., ATxmega384C3) to receive force and torque feedback from the end effector and generate a digital disable command to the robot if the force or torque exerted on the patient reaches or exceeds a safety threshold. The embedded system also captures enable/disable input from the user and generates commands to the robot. The embedded system uses a Main Loop unit designed to provide round-robin and scheduling between software units. An ADC unit controls the Analog to Digital conversion hardware interface unit. A Force Calculation unit converts all voltages acquired by the ADC unit into force and torque values. A Robot Relay Control unit generates a disable signal for the robot if the force or torque exerted on the patient reaches or exceeds a predetermined threshold.

In some embodiments, the safety features of the software system architecture include one or both of the following.

Force Threshold Stop: Both the LabVIEW Control System and the Embedded Safety System can acquire force and torque signals from the F/T sensor, and can restrict UR5 motion in the event that set thresholds are reached or exceeded. The LabVIEW Control System can compare force to conservative "warning" thresholds and, if reached or exceeded, the system can adjust its processing to stop motion control in the force-increasing direction(s), but allow motion control in the force-decreasing direction(s), so that the physician can disengage the system and reduce force. The Embedded Safety System can compare force to a safety threshold that is higher that the "warning" threshold and, if reached or exceeded, an emergency signal to the Safety Controller unit of the UR5 can be activated, which can disable all control of the UR5 arm until the system is manually re-enabled by the physician.

Safeguard Enable/Disable: To protect against unintended movement at critical points (e.g., during cutting), the embedded safety system can include a pushbutton switch that toggles between Enable and Disable modes, which can be indicated by an Enable/Disable LED. At the appropriate times, the physician can disable motion capabilities of the uterine manipulation system by toggling the pushbutton to put it in disabled mode. In this mode an output signal is generated by the Robot Relay Control, triggering a relay in the Safety Controller of the UR5 robot, which causes Motion or Freedrive commands from LabVIEW to be ignored.

Software System Items and Units

Figure 13:
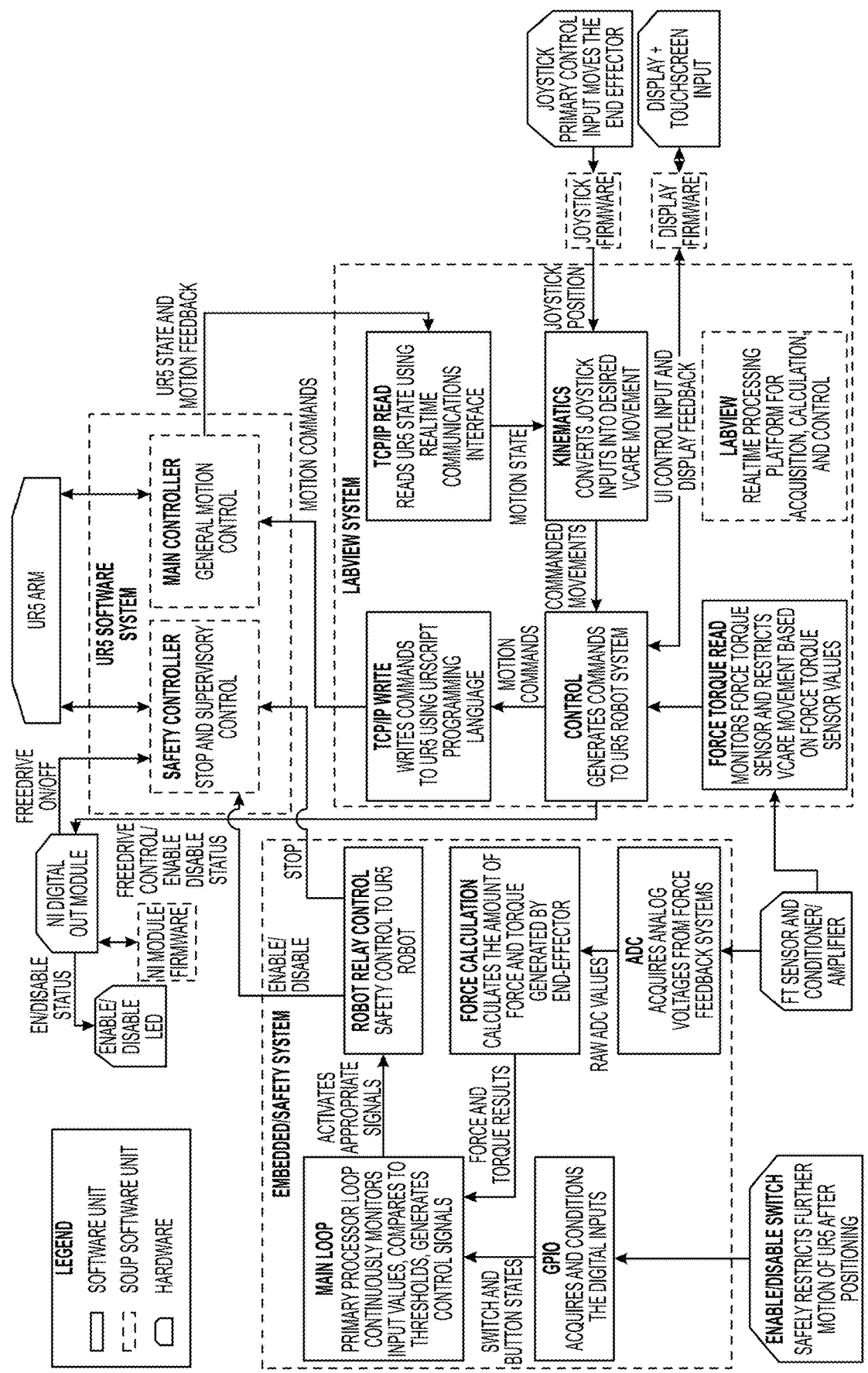
FIG. 13 is a diagram of a software system architecture, according to various embodiments of the invention.

FIG. 13 shows a software system architecture according to an illustrative embodiment of the present invention. The primary custom software components are the "Embedded/Safety System" that monitors force and/or torque and disables the robot if a threshold is exceeded, and the "LabVIEW System" that provides real-time control of the UR5 robotic arm. Each of the top-level software items is broken down into individual software units as shown in FIG. 14. Example 1 further describes the Embedded/Safety System and Example 3 provides further detail on each of its supporting units. Example 2 further describes the LabVIEW System and Example 4 provides further detail on each of its supporting units. With reference to FIGS. 13 and 14:

In the "LabVIEW System" ("LabVIEW Control") the "Control" unit provides central coordination of the LabVIEW units; this unit receives user input from "Kinematics," "Force Torque Read," and the user interface through the display, and generates the commands to the robot. The "Kinematics" unit converts joystick inputs into desired uterine manipulator movement. The "Force Torque Read" unit monitors the F/T sensor and restricts uterine manipulator movement based on F/T sensor values. The "TCP/IP Read" unit reads the UR5 state using the UR5 real-time communications interface. The "TCP/IP Write" unit writes commands to the UR5 using URScript Programming Language. "LabVIEW" is the real-time processing platform for acquisition, calculation, and control. "Joystick Firmware" is firmware in the joystick that translates position into electrical signals. "Display Firmware" ("Touchscreen Firmware") is firmware in the touchscreen that provides control and touch processing. "NI Module Firmware" is firmware in the NI Digital Output Module.

In the "Embedded/Safety System" the "Main Loop" is an infinite loop that provides time-based functionality and coordination for other units. The "GPIO" (general-purpose input/output) unit acquires and conditions digital inputs from the Enable/Disable Switch. The "ADC" (analog-to-digital converter) unit acquires voltage readings from each of the six channels of force and torque generated by the F/T sensor. The "Force Calculation" unit converts measured voltages from the F/T sensor to force and torque measurements. The "Robot Relay Control" unit provides control of the robot power relay; the Digital I/O output can enable/disable the robot by connecting/removing power from the system.

In the "UR5 Software System" the "Main Controller" provides coordinated motion control of the UR5 robotic arm. The "Safety Controller" is supervisory firmware on the motion control outputs of the UR5 Main Controller; this firmware receives enable/disable inputs and emergency stop, and controls power output to the robot motor controller.

In some embodiments, "SOUP" software units that can be used in the illustrative software system architecture are as follows. "LabVIEW" may comprise, for example, National Instruments LabVIEW 2016 v16.0. "Joystick Firmware" may comprise, for example, APEM HF46S10U HID game controller 6.1.7601.1899. "Touchscreen Firmware" may comprise, for example, Gechic On-Lap 1503I 358B10L5T0309. "NI Module Firmware" may comprise, for example, National Instruments NI-9485 MAX 17.0. The UR5 "Main Controller" may comprise, for example, UR5 3.4.1.59. The UR5 "Safety Controller" may comprise, for example, UR5 URSafetyA 504 and URSafetyB 256. In other embodiments, different versions and/or different software units may be used, depending on the specific robot arm, joystick, display, and software development environment selected.

System Calculations

Force/Torque: In some embodiments, when manipulation is occurring, the system continuously monitors force and torque readings. The three components of force and torque (Fx, Fy, Fz, Tx, Ty, Tz) are combined into one force magnitude and one torque magnitude. Limits on force and torque (e.g., the LabVIEW and Embedded Safety Force and Torque Thresholds described above) are preset within the software (and are preferably independent of each other). It should be noted that in certain embodiments, different force and/or torque thresholds may be set for different movements. Once either force or torque reaches its preset limit, a "trip" switch is flipped in the logic of the controller, and the manner of manipulation in which the limit was exceeded (e.g., in any direction or combination, such as pitch upward, forward translation, etc.) is saved. With the trip enabled, the user may use the "Home" button on the user interface, or may use the joystick, to move in the opposite direction of the movement that caused the trip. For example, if a forward translation caused a force or torque limit to be exceeded, the only movements allowed may be Home or backward translation. Any other joystick inputs would be ignored by the controller and the robot would not move. The trip is only disabled once the force and torque have decreased to some margin below the preset limit. For instance, if a force limit of 7 lbf is exceeded and the trip enabled, the trip would not be disabled until the force has decreased to below 5 lbf (a two pound margin). This deadband (margin) prevents minor fluctuations in the measurements from affecting the status of the trip, and requires the user to take distinct action to disable the trip. Once the trip has been disabled, movement constraints are released and normal operation is resumed, including in the direction that caused the trip.

Pitch/Yaw: In some embodiments, pitch and yaw movements are calculated as follows. At each iteration of the kinematics module (which preferably runs at 10 Hz), pitch and yaw inputs are read from the joystick (in the present embodiment, if a translation input is received, pitch and yaw inputs are ignored.) A relatively small pitch and yaw are chosen to calculate a new manipulator tip location. Using small increments results in smooth robot arm motion (a better approximation of a curve). A new manipulator handle location and orientation (i.e., robot arm location and orientation) are then calculated that would place the tip in the new location and keep the manipulator aligned with the fulcrum. The new calculated robot arm location and orientation are compared to the current location and orientation to generate a movement velocity vector. The uterine manipulation system controller sends a command to the UR5 to move along the specified vector at a specified speed. This command is updated 10 times per second, resulting in a series of vectors that approximate the desired curve of motion.

Translation: In some embodiments, translation movements are calculated in a manner similar to pitch/yaw movements. At each iteration of the kinematics module, a trajectory is generated that passes through both the fulcrum and the tip of the uterine manipulator. This is the line along which translation will occur, as illustrated in FIG. 12. The translation direction (e.g., either forward/into the uterus or backward/out of the uterus) is read from the joystick. The new handle/robot arm location and orientation are then calculated in two steps. First, the entire uterine manipulator is assumed to shift (i.e., orientation does not change) in order to place the manipulator tip in the new location. However, this causes the manipulator to become misaligned from the fulcrum. Second, the manipulator is assumed to rotate about the new tip location so that the manipulator becomes realigned with the fulcrum. The new calculated robot arm location and orientation from these two steps are then compared to the current location and orientation to generate a velocity vector, which is sent to the UR5 as a command and is updated 10 times per second.

EXAMPLES

Example 1: Embedded/Safety System

In some embodiments, the Embedded/Safety System is configured as follows.
1.1—Hardware Platform The controller board is an ATMEL XMEGA-C3 development board. The controller board utilizes an Atmel ATxmega384C3 8/16-bit microcontroller operating at 32 MHz via an internal oscillator. The internal timers use 32 MHz as their base frequency, dividing it down as required. Firmware developed for this microcontroller performs all of the real-time control and monitoring functions required by this device. There is no operating system used in this microcontroller.

The microcontroller contains a Watchdog timer that is configured to reset the processor if the software hangs or does not meet its execution time.

An IEEE 1149.1 compliant JTAG interface is available on the embedded board of the uterine manipulator device to program and to perform debugging of the microprocessor. This JTAG interface allows the developer to load the microprocessor's application program and the bootloader program as well as set or clear the Atmel AVR ATxmega384C3 bits for locking and protecting the firmware, brownout detection, bootloader flash address range, JTAG enable, watchdog enable, etc. The JTAG interface is only used in development and is not accessible by the end user.
1.2—Main Loop The microprocessor firmware program is structured around a service loop. The service loop is driven by an internal 16-bit timer which interrupts the AVR processor 100 times per second. The purpose of the main loop is to initialize the units, then provide precise timing for the various tick functions of the composite units.

The 100 Hz service loop resets a watchdog timer in each of its executions. During initialization of the software, the processor STATUS register is checked to see if the reset was due to watchdog timer elapsing. If so, the robot is put into a safe state (Safeguard and Emergency relays open) and further code execution is prevented, thus preventing use of the robot.
1.3—Finite State Machine FIG. 14 describes the states and transitions that comprise the embedded safety system finite state machine (FSM).

On power-up the first state is the initialization state. The ADC software unit interfaces with an external analog-to-digital conversion chip that has a specific timing sequence required to initialize it. The overall FSM stays in the initializing state, until the ADC unit initialization is successful. The enable/disable output to the UR5 robot is enabled to allow the UR5 robot to initialize and user to setup the robot.

The unit stays in monitoring state for the majority of the device operation. During this state the lower-level units monitor force and torque as well as allow the user to enable and disable the robot.

A fault at any time will result in a transition to the Fault state. Conditions that lead to a fault include unexpected states in the overall finite state machine, unexpected ADC unit internal finite state machine, and excessive force or torque values.

The FSM has no inherent timing considerations, it simply monitors signals from the other units (primarily buttons and various process data sources) and then issues commands to units accordingly. It is the responsibility of the commanded units to space out their activities with respect to time. The FSM is executed outside and after the service loop, on every iteration of the infinite loop, in order to process and respond to new user input or detected conditions as quickly as possible.
1.4—Supporting Units See Example 3 for a detailed description of each of the supporting units that manage subsystems and are coordinated by the Main Loop unit.

Example 2: LabVIEW System

In some embodiments, the LabVIEW System is configured as follows.
2.1—Hardware Platform The LabVIEW hardware comprises a LabVIEW computer and a LabVIEW hardware controller.

The LabVIEW computer is a Windows 7 computer (Dell Optiplex 3050) running a custom LabVIEW VI (Virtual Instrument) on top of a run time engine of LabVIEW 2016. The LabVIEW computer generates an HDMI output to interface with the touch screen panel, a USB interface to communicate with the LabVIEW hardware controller, and an Ethernet port to communicate with the UR5 robot.

The LabVIEW hardware controller (National Instruments cDAQ-9174) provides an interface between the LabVIEW computer and hardware modules (NI-9205 and NI-9485). Hardware module NI-9205 is an analog voltage input module that is used to digitize force and torque signals from the ATI-IA F/T sensor on the end effector. Similarly, hardware module NI-9485 provides a Solid-State Relay that controls Freedrive and Enable/Disable input of the UR5 robot.

2.2—Architecture

The custom LabVIEW VI contains multiple units executing in parallel loops with data and states communicated between loops. The top level units that run in parallel are listed with hierarchy shown below. Control and Force-Torque Read units are loops that contain subsequent units. TCP Write, Kinematics, and TCP Read are SubVIs that reside within the higher level Control unit.

Control
    TCP Write
        Kinematics
    TCP Read
Force-Torque Read 2.3—Control The Control unit is primarily responsible for control of the UR5 robot. The control unit gets user input through a GUI (e.g., as shown in FIG. 15). The Control unit also receives user position input through a joystick. The inputs are processed in a loop executing at 10 milliseconds. The Fulcrum Position (e.g., in cm) is entered based on the patient-specific distance measured on the uterine manipulator. This patient-specific distance will change the geometry and handle motion.

The inputs are used to affect the state of the UR5 robot. The Kinematics unit is provided with the user position inputs. Corresponding changes to the UR5 robot are commanded through the TCP Write unit. The TCP Write unit generates commands to the UR5 to change state or position. The Control unit reads the status of the UR5 robot through the TCP Read unit which parses feedback from the robot.

The Control unit also generates a log file containing the position and states of the UR5 robot.

The LabVIEW VI has five states that govern its behavior: Init, Freedrive, Write Data/Manipulation, Not Normal, and Close.

Init: This is the initial state of the LabVIEW software. The log file is created and variables are commanded their initial states. The state transitions either to Freedrive state or to Write Data/Manipulation state.

Freedrive: This state is entered after initialization and when the user commands the drive mode to be in Freedrive Mode. On the first call only, this state initializes the joystick firmware. The UR5 robot is commanded to be Freedrive Mode. This state is maintained until the user changes to Manipulation Mode on the UI, closes the UI, or the feedback from the UR5 robot indicates abnormal state.

Write Data/Manipulation: This state is entered when the user sets the drive mode to be in Manipulation Mode. The joystick states are read, passed along to the Kinematics unit, and ultimately used by TCP Write to send commands to the UR5 robot. The TCP Read unit is also executed to monitor the status of the robot.

Not Normal: This state is entered when the UR5 robot feedback as parsed by the TCP Read unit returns an unexpected state. In response, the robot is commanded to be in a safe state. The state is also logged.

Close: This state is entered when the user closes the application. All resources are appropriately released including the log file.

2.4—Force Torque Read

The Force Torque Read unit configures NI-9205 to acquire six channels of analog voltages at 1000 samples per second. These analog channels are wired to the output of the ATI-IA Mini40 three-axis F/T sensor output. The acquired voltages are converted to lbf and lbf-in for force and torque channels, respectively.

2.5—Supporting Units

See Example 4 for a detailed description of each of the supporting units.

Example 3: Supporting Units for Embedded/Safety System

In some embodiments, the remaining units of the Embedded/Safety System are as shown in Table 1.

TABLE 1

| Subsystem | Unit |
|---|---|
| Force | ADC Unit |
|  | Force Unit |
| Robot Relay Control | Relay Unit |
| GPIO | GPIO/Buttons Unit |

3.1—ADC Unit

Overview The ADC unit communicates via Serial Peripheral Interface (SPI) to the Analog Devices AD7616 Analog-to-Digital conversion chip. The ADC chip acquires data from the ATI-IA three-axis F/T sensor at a rate of 100 samples/second.

Public Interface

Table 2 describes the ADC public methods, including any objects or data items passed from the unit that will be used by other software units.

TABLE 2

| Category | Method | Description |
|---|---|---|
| Initialization | void ADC_init( ) | Initializes data, SPI communication, and resets IO interface to ADC. |
| Data | void get_adc_average(uint16_t * force_torque_buffer) | Populates the current average values of the 200 point running averages for each of the six force and torque axis. |
|  | unsigned char is_adc_in_fault_state(void) | Returns true if ADC fsm is in fault state, false otherwise. |
| Tick | void ADC_100 Hz_tick( ) |  |

Normal Operation

The ADC Unit has an internal FSM to properly initialize the AD7616 IC. The sequence of operation transitions through the states listed below:

STATE_WAIT_FOR_RESET: Reset pin on the AD7616 is activated on entry to this state. 20 milliseconds is allowed to elapse prior to further initialization with the IC. Once the 20 ms expires, the unit transitions to STATE_SET_REGISTERS.

STATE_SET_REGISTERS: During the first execution of this state, the unit sends a SPI command to set the configuration register of the ADC. During the second execution, the unit sets the end of the sequence register.

STATE_INITIAL_PSEUDO_ACQ: The first conversion of the ADC is expected to be meaningless. This state of the FSM acquires the first conversion and throws away the data.

STATE_ACQUISITION: Voltages are acquires for the six channels of voltage.

STATE_ADC_FAULT: Unexpected input from ADC results in transition to this state.

3.2—Force Unit

Overview

The Force unit communicates with the ADC unit and receives the raw voltages received from the ATI-IA F/T sensor. The unit converts the raw voltages to force and torque values based on the manufacturer provided calibration information.

Public Interface

Table 3 describes the Force unit public methods.

TABLE 3

| Category | Method | Description |
| --- | --- | --- |
| Initialization | void initialize_force(void) | Initializes data |
| Data | unsigned char is_force_torque_limit_exceeded | Returns true if the embedded limit for force or torque have been exceeded. |
| Tick | void ADC_100_Hz_tick( ) | |

Normal Operation

The Force unit acquires an average of 10 data points (samples rate: 100 Hz; average window: 10 ms) for the following channels:
  Force in X-Axis
  Force in Y-Axis
  Force in Z-Axis
  Torque in X-Axis
  Torque in Y-Axis
  Torque in Z-Axis The raw voltages are converted to force and torque utilizing a matrix of values provided by the manufacturer specified in the data section below.

The Force unit also monitors each force and torque channel (voltage) to ensure they are below force and torque limits as set for the specific anatomical manipulation.

Data

The ATI-IA Mini40 three-axis F/T sensor is provided with a calibration table to convert the six voltage readings (Fx, Fy, Fz, Tx, Ty, Tz) into calibrated force and torque values in lbf and lbf-in, respectively. The conversion (calibration) table is provided below in Table 4. This data is excerpted from ATI Certificate Number FT21031-20171219.

TABLE 4

| | G0 | G1 | G2 | G3 | G4 | G5 |
| --- | --- | --- | --- | --- | --- | --- |
| Fx | 0.03969 | 0.00863 | −0.00157 | 2.81851 | 0.03457 | −2.81663 |
| Fy | −0.05164 | −3.26139 | 0.10099 | 1.62774 | −0.00610 | 1.62747 |
| Fz | 4.79715 | −0.19268 | 4.78857 | 0.20282 | 4.76946 | −0.17657 |
| Tx | −0.03523 | −0.67952 | 2.70142 | 0.44584 | −2.72734 | 0.43822 |
| Ty | −3.10760 | 0.13889 | 1.58020 | −0.53137 | 1.57522 | 0.52792 |
| Tz | −0.00253 | −1.51986 | −0.02933 | −1.53482 | 0.01123 | −1.54086 |

The calibration conversion is performed by matrix multiplication between a vector of voltages ([Fx, Fy, Fz, Tx, Ty, Tz]) and the calibration matrix listed in Table 4.

3.3—Relay Unit

Overview

The Relay unit abstracts the relays used to control the UR5 Robot Safeguard and Emergency Break inputs.

The Robot Safeguard input is used to control whether motion is enabled/disabled during normal operations based on operator input. An "enable" function call (to enable_safeguard_relay( )) pulls the corresponding IO to a logic level high, which enables motion in the UR5 robot. Alternatively, a "disable" function call (to disable_safeguard_relay( )) pulls the corresponding IO to a logic level low, which brings motion in the UR5 robot to a controlled stop. A "toggle" function call (to toggle_safeguard_relay( )) changes the current state from disabled to enable or vice versa.

The Robot Emergency Break input is used to immediately stop all robot motion. An "enable" function call (to enable_emergency_relay( )) pulls the corresponding IO to a logic level high, which enables motion in the UR5 robot. Alternatively, a "disable" function call (to disable_emergency_relay( )) pulls the corresponding IO to a logic level low, which immediately disables all motion in the UR5 robot.

Public Interface

Table 5 describes the Relay unit public methods.

TABLE 5

| Category | Method | Description |
| --- | --- | --- |
| Initialization Data | void init_relay( ) | Enables both safeguard and emergency relays |
| | void enable_safeguard_relay( ) | Sets IO corresponding to safeguard relay. |
| | void disable_safeguard_relay( ) | Clears IO corresponding to safeguard relay. |
| | void toggle_safeguard_relay( ) | Toggles the state of the safeguard relay |
| | void enable_emergency_relay( ) | Sets IO corresponding to emergency relay |
| | void disable_emergency_relay( ) | Clears IO corresponding to emergency relay |

Normal Operation

On initialization, the unit enables both Safeguard and Emergency relays. Subsequently, the unit enables and disables outputs according to the public methods listed above.

Data

Table 6 describes the Relay unit data.

TABLE 6

| IO Function | Port, Pin | |
| --- | --- | --- |
| Safeguard Relay Control IO | PORT B, Pin 0 | Enabled = HIGH = motion allowed |
| Emergency Relay Control IO | PORT B, Pin 1 | Enabled = HIGH = motion allowed |

3.4—GPIO/Buttons Unit

Overview

The GPIO unit abstracts the user pushbutton ("Safeguard button"). The unit uses a 50 Hz tick to sample the button to provide de-bouncing. The unit provides high level query functionality to indicate whether the pushbutton has been pressed since last checked.

Public Interface

Table 7 describes the GPIO/Buttons unit public methods.

TABLE 7

| Category | Method | Description |
|---|---|---|
| Initialization | void init_buttons( ) | Initializes data |
| Data | void clear_button_flags( ); | Resets the state of all buttons |
| | unsigned char has_been_pressed (enum e_button btn) | Returns whether the selected button has been pressed since last check |
| Tick | void button_tick_50 Hz( ); | 50 Hz tick |

Normal Operations

Unit monitors Safeguard pushbutton input for user presses.

Data

Table 8 describes the GPIO/Buttons unit data.

TABLE 8

| IO Function | Port, Pin |
|---|---|
| Safeguard Pushbutton Input | PORT E, Pin 1 |

Example 4: Supporting Units for LabVIEW System

This Example describes the following supporting units for the LabVIEW System "Control" unit/subsystem: Kinematics Unit, TCP Read, and TCP Write.

4.1—Kinematics Unit

Overview

The Kinematics unit receives the inputs listed below and calculates and commands a corresponding robot position:
  Joystick input
  Current robot position
  Kinematics initialization positions: Setup or home position and orientation of robot. The setup/home position of the robot is recorded when the operator switches from Freedrive to Manipulation Mode.

Logic

Kinematics code according to an illustrative embodiment is provided in the computer program listing appendix, which is incorporated by reference herein in its entirety. The kinematics code of embodiments of the present invention is specific to the geometry of the particular end effector held/manipulated by the robot, as well as the anatomy of the individual patient (e.g., the patient-specific distance from tip to fulcrum of the uterine manipulator, as described above). Various existing tools for use with surgical robots are straight, and thus have relatively straightforward kinematics. In contrast, tools for uterine manipulation, such as the VCare®, are curved, and have an adjustable fulcrum that is patient-specific; the kinematics code of embodiments of the present invention includes logic for controlling the end point of such tools and providing smooth movement for anatomical manipulation during surgical procedures. In the present embodiment, there is a hardcoded offset of about a few inches in the logic that accounts for the F/T sensor thickness and the depth of the back of the mechanical interface (i.e., the distance between the end of the manipulator handle and the distal end of the robot arm). In the logic, this extra distance is added to the length of the manipulator tool, effectively making the tool appear longer and thus accounting for the distance in the calculation of movement vectors.

Parameters in the illustrative kinematics code include: "L", which is the length from robot tool to VCare® tip along VCare® handle axis (cm); "tipY"/Tip Elevation (cm), which is the distance from the robot tool (distal end) to the VCare® tip normal to the VCare® handle axis; "ful_pos_pat"/Fulcrum Position (cm), the patient-specific distance measured from the graduation marks on the VCare®, which indicates the position of the cervix through execution (can be reinitialized); "theta_max"/Max Optimization Speed (deg/sec), which is the maximum speed that limits how fast corrections can occur; and "dist_lookup"/Distance Lookup Table (cm), which is a lookup table used to correlate VCare® coordinates to the patient-specific distance from the fulcrum from the tip. For performing a pitch/yaw motion, additional parameters include: "dt"; "pitch_max"/Max Pitch Speed (deg/sec); and "yaw_max"/Max Yaw Speed (deg/sec). For performing a distance move, additional parameters include: "dD" (cm), which is an incremental distance used to plot the trajectory for the distance move; "minSpeed_dist"/Min Distance Speed (cm/s), which is the distance speed corresponding to minimum speed toggle; and "maxSpeed_dist"/Max Distance Speed (cm/s), which is the distance speed corresponding to maximum speed toggle. A distance (translation) move is performed by selecting a new point for the VCare® tip along the straight line from the fulcrum to the tip. As noted above, in order to calculate a new translated position of the VCare®, the code first "translates" the VCare® so that the tip is in the new location, and then "rotates" the VCare® about the new tip location so that the new fulcrum position on the VCare® returns to the fixed cervix. The end position and orientation of the handle based on the calculations is used to give to robot commands, so both the translation and rotation motions occur simultaneously.

In some embodiments, the kinematics code includes four modules as described below: KINEMATICS INITIALIZE, PRE KINEMATICS, KINEMATICS—PITCH/YAW, and KINEMATICS—DISTANCE.

KINEMATICS INITIALIZE: This code only runs once each time Manipulation Mode is entered. It sets parameters based on the initial orientation of the robot that are used by the Kinematics modules on each iteration.

PRE KINEMATICS: This code runs each iteration (10 times per second) while in Manipulation Mode. It reads the current orientation of the robot and calculates geometric parameters that are used by the Kinematics modules.

KINEMATICS—PITCH/YAW: This code runs each iteration (10 times per second) while in Manipulation Mode if a pitch/yaw command is received. It reads the current joystick command (filtered by force/torque input and other controls), current robot state output from Pre Kinematics, and initialized parameters from Kinematics Initialize, and calculates the appropriate speed command to send to the robot. It also performs some simple closed-loop control designed to keep the VCare® from pulling too much on the patient at the insertion point (the cervix). Lastly, the code performs an "optimization" step designed to keep the VCare® handle from moving too far laterally from its initial position. If it does move too far laterally, the robot can reach the edges of its range.

KINEMATICS—DISTANCE: This code runs each iteration (10 times per second) while in Manipulation mode if a distance (translation) command is received. It reads the current joystick command (filtered by force/torque input and other controls), current robot state output from Pre Kinematics, and initialized parameters from Kinematics Initialize, and calculates the appropriate speed command to send to the robot.

4.2—TCP Read Unit

The TCP Read unit parses feedback received from the UR5 robot.

4.3—TCP Write Unit

The TCP Write unit transforms UR5 robot commands into the syntax expected by the UR5 controller.

While there have been shown and described fundamental novel features of the invention as applied to the preferred and illustrative embodiments thereof, it will be understood that omissions and substitutions and changes in the form and details of the disclosed invention may be made by those skilled in the art without departing from the spirit of the invention. Moreover, as is readily apparent, numerous modifications and changes may readily occur to those skilled in the art. For example, various features and structures of the different embodiments discussed herein may be combined and interchanged. Hence, it is not desired to limit the invention to the exact construction and operation shown and described and, accordingly, all suitable modification equivalents may be resorted to falling within the scope of the invention as claimed. It is the intention, therefore, to be limited only as indicated by the scope of the claims appended hereto.

What is claimed is:

1. A robotic anatomical manipulation system for use with an end effector configured to position and hold an anatomy of a patient during a minimally invasive surgical procedure, the system comprising:
    a robot comprising a cart and an arm, a proximal end of the arm connected to the cart, the arm having a plurality of joints configured for multiple ranges of motion;
    a console comprising a joystick and a user interface, the joystick configured to provide real-time motion inputs to the arm;
    a mechanical interface connected to a distal end of the arm and configured to releasably retain a proximal end handle of the end effector external to the anatomy of the patient, wherein the end effector has an elongated body having a shape configured for insertion into and to conform to a portion of the anatomy of the patient, a distal end tip, and an adjustable fulcrum configured to be positioned at a distance relative to the distal end tip that is specific for the portion of the anatomy of the patient;
    a sensor disposed between the distal end of the arm and the mechanical interface, wherein the mechanical interface is configured to transfer at least one of force and torque from the end effector to the sensor, and wherein the sensor is configured to measure the at least one of force and torque along each of three axes; and
    a control system in communication with the arm, the console and the sensor, the control system comprising a computer processor configured for executing a program stored in a non-transitory computer readable medium for controlling the arm responsive to user input through the joystick and the user interface, the control system further comprising:
        a kinematics unit configured to receive input from the joystick and the sensor and generate control commands to control motion of the arm to produce user-specified motion of the tip based on a current position of the arm, a shape of the end effector, and a patient-specific fulcrum position of the end effector, wherein the control commands comprise one or a combination of translation, translation speed, rotation, rotation speed, pitch, yaw, enable, and disable; and
        an embedded safety system comprising a force/torque read unit configured to continuously monitor the at least one of force and torque detected by the sensor and calculate a magnitude of the at least one of force and torque and to provide a signal comprising the calculated magnitude to the user interface, wherein the embedded safety system is further configured to compare the calculated magnitude to one or more predetermined threshold, and if the one or more predetermined threshold is exceeded, to generate a disable command to disable arm motion within all or a subset of the multiple ranges of motion.

2. The system of claim 1, wherein the anatomy is a uterus and the end-effector comprises a uterine manipulator.

3. The system of claim 1, wherein the console further comprises a video feed configured to display a live signal from a camera used to monitor the surgical procedure.

4. The system of claim 1, wherein the arm comprises six joints: base (A), shoulder (B), elbow (C), and wrist (D, E, F).

5. The system of claim 4, wherein the elbow is positioned below the wrist in a baseline position.

6. The system of claim 1, wherein the arm comprises at least one joint having markings thereon, the markings indicating safe ranges for a baseline position.

7. The system of claim 1, wherein the mechanical interface includes a quick release mechanism configured to release the end effector without moving the robot arm or cart.

8. The system of claim 1, wherein the sensor is configured to acquire six channels of force and torque: Fx, Fy, Fz, Tx, Ty, and Tz.

9. The system of claim 1, wherein the one or more threshold comprises one or more of a warning force threshold, a safety force threshold, a warning torque threshold, and a safety torque threshold.

10. The system of claim 1, wherein the embedded safety system comprises an analog-to-digital converter (ADC) unit configured to acquire force and torque data from the sensor at least 100 times per second.

11. The system of claim 10, wherein the embedded safety system further comprises a force unit configured to receive raw voltages communicated by the sensor to the ADC unit, and to convert the raw voltages to force and torque values.

12. The system of claim 1, wherein the console includes a mechanism to enable/disable control of the arm from the joystick and the user interface, and wherein the embedded safety system generates a command to the robot responsive thereto.

13. The system of claim 1, wherein the user interface includes a stop axis indicator configured to provide a visual indication indicating an axis along which the one or more predetermined threshold was exceeded.

14. The system of claim 1, wherein the cart further comprises a setup positioning system on an upper surface thereof, the proximal end of the arm connected to the setup positioning system, and the setup positioning system configured to provide forward and reverse translation in the X, Y, and Z directions.

15. The system of claim 1, wherein the control system is further configured to generate an alarm providing an audible indication of at least one of movement and speed of the distal end of the arm.

16. The system of claim 1, wherein the disable command limits arm motion in a direction at which the one or more predetermined threshold was exceeded and allows arm motion in an opposite direction.

17. The system of claim 16, wherein user control of arm motion is fully enabled after the calculated magnitude decreases below the one or more predetermined threshold.

18. A robotic system for manipulation of an end effector configured to position and hold an anatomy of a patient, the system comprising:
- a robot comprising an arm having a proximal end mounted on a support base and a distal end, the arm configured for multiple ranges of motion using a plurality of joints disposed between the proximal end and the distal end;
- a user interface in communication with the arm, the user interface configured to provide real-time motion inputs to the arm;
- a mechanical interface disposed at the distal end of the arm, the mechanical interface configured to releasably retain a proximal end handle of the end effector, the end effector having an elongated body extending from the proximal end handle and a shape configured for insertion into and to conform to a portion of the anatomy of a patient, a distal end tip, and an adjustable fulcrum disposed between the handle and the distal end tip, the fulcrum configured to be positioned at a distance relative to the distal end tip that is specific for the portion of the anatomy of the patient;
- a sensor disposed between the distal end of the arm and the mechanical interface, wherein the mechanical interface is configured to transfer at least one of force and torque from the distal end tip of the end effector to the sensor, and wherein the sensor is configured to measure the at least one of force and torque along each of three axes;
- a control system in communication with the arm, the console and the sensor, the control system comprising a computer processor configured for executing a program stored in a non-transitory computer readable medium for controlling the arm responsive to user input through the user interface, the control system further comprising:
  - a kinematics unit configured to receive input from the user interface and the sensor and to generate control commands to control motion of the arm to produce user-specified motion of the tip based on a current position of the arm, the shape of the end effector, and a patient-specific fulcrum position of the end effector, wherein the control commands comprise one or a combination of translation, translation speed, rotation, rotation speed, pitch, yaw, enable, and disable; and
  - an embedded safety system comprising a force/torque read unit configured to continuously monitor the at least one of force and torque detected by the sensor and calculate a magnitude of the at least one of force and torque and to provide a signal comprising the calculated magnitude to the user interface, wherein the embedded safety system is further configured to compare the calculated magnitude to one or more predetermined threshold, and if the one or more predetermined threshold is exceeded, to generate a disable command to disable arm motion within all or a subset of the multiple ranges of motion; and
- a display in communication with the control system, the display configured for displaying the calculated magnitude and one or more of a position of the arm, a status of the kinematics unit, and a status of the embedded safety system.

19. The system of claim 18, wherein the anatomy is a uterus and the end-effector comprises a uterine manipulator.

20. The system of claim 18, wherein the plurality of joints comprises six joints: base (A), shoulder (B), elbow (C), and wrist (D, E, F).

21. The system of claim 18, wherein the support base comprises a movable and lockable cart.

* * * * *